(12) United States Patent
Maher et al.

(10) Patent No.: US 12,343,435 B2
(45) Date of Patent: Jul. 1, 2025

(54) WOUND CARE DEVICE HAVING FLUID TRANSFER AND ADHESIVE PROPERTIES

(71) Applicant: Milliken & Company, Spartanburg, SC (US)

(72) Inventors: Laura Maher, Campobello, SC (US); Matthew I. Foote, Spartanburg, SC (US); Gregory A. Satterfield, Pelzer, SC (US); Rajib Mondal, Greer, SC (US); Cristina M. Acevedo, Greer, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 17/686,597

(22) Filed: Mar. 4, 2022

(65) Prior Publication Data
US 2022/0184269 A1 Jun. 16, 2022

Related U.S. Application Data

(62) Division of application No. 16/415,073, filed on May 17, 2019.
(Continued)

(51) Int. Cl.
*A61L 15/58* (2006.01)
*A61F 13/00* (2024.01)
(Continued)

(52) U.S. Cl.
CPC ...... *A61L 15/585* (2013.01); *A61F 13/00063* (2013.01); *A61F 13/0206* (2013.01);
(Continued)

(58) Field of Classification Search
CPC ...... A61L 15/585; A61L 15/18; A61L 15/225; A61L 15/24; A61L 15/44; A61L 15/58;
(Continued)

(56) References Cited

U.S. PATENT DOCUMENTS 2,764,976 A   10/1956   Skiles, Jr.
3,292,619 A   12/1966   Egler
(Continued)

FOREIGN PATENT DOCUMENTS

DE   102016008257 A1   1/2018
WO   2007113597 A2   10/2007
(Continued)

OTHER PUBLICATIONS

Patent Cooperation Treaty PCT International Search Report. Date of Mailing, Nov. 13, 2019. International Application No. PCT/US2019/033103. International Filinq Date: Jul. 8, 2019.

*Primary Examiner* — Kai H Weng
*Assistant Examiner* — Kate Elizabeth Strachan
(74) *Attorney, Agent, or Firm* — Brenda D. Amidon

(57) ABSTRACT

This disclosure relates to a wound care device which contains capillary force one-way pumps that are capable of transporting fluid, such as wound exudate, away from a wound site to the opposite side of the wound care device, which functions as a segregated fluid reservoir. This fluid transport mechanism generally aids in reducing wound maceration by removing excess wound fluid and the protease enzymes and infectious bacteria contained within the wound fluid. The wound care device performs this function, often times for multiple days, without the loss of the physical integrity of the wound care device. In addition to providing a uni-directional fluid transport mechanism, the wound care device contains a perforated adhesive layer.

18 Claims, 12 Drawing Sheets

Related U.S. Application Data

(60) Provisional application No. 62/674,095, filed on May 21, 2018.

(51) Int. Cl.
*A61F 13/0203* (2024.01)
*A61F 13/0206* (2024.01)
*A61L 15/18* (2006.01)
*A61L 15/44* (2006.01)

(52) U.S. Cl.
CPC ...... *A61F 13/0209* (2013.01); *A61F 13/0213* (2013.01); *A61L 15/18* (2013.01); *A61L 15/44* (2013.01); *A61F 2013/00119* (2013.01); *A61F 2013/00217* (2013.01); *A61F 2013/00238* (2013.01); *A61F 2013/00319* (2013.01); *A61F 2013/00323* (2013.01); *A61L 2300/104* (2013.01); *A61L 2300/404* (2013.01)

(58) Field of Classification Search
CPC ......... A61L 2300/104; A61L 2300/404; A61F 13/00063; A61F 13/0206; A61F 13/0209; A61F 13/0213; A61F 13/0253; A61F 2013/00119; A61F 2013/00217; A61F 2013/00238; A61F 2013/00319; A61F 2013/00323
See application file for complete search history.

(56) References Cited

U.S. PATENT DOCUMENTS

| | | |
|---|---|---|
| 4,541,426 A | 9/1985 | Webster |
| 4,603,076 A | 7/1986 | Bowditch |
| 4,614,183 A | 9/1986 | Mccracken |
| 4,635,624 A | 1/1987 | Gilman |
| 4,664,106 A | 5/1987 | Snedeker |
| 4,684,557 A | 8/1987 | Pennace |
| 4,738,257 A | 4/1988 | Meyer |
| 4,750,482 A | 6/1988 | Sieverding |
| 4,753,231 A | 6/1988 | Lang |
| 4,762,680 A | 8/1988 | Pennace |
| 4,838,253 A | 6/1989 | Brassington |
| 4,846,164 A | 7/1989 | Martz |
| 4,860,737 A | 8/1989 | Lang |
| 4,921,704 A | 5/1990 | Fabo |
| 4,950,148 A | 8/1990 | Nakanishi |
| 4,977,892 A | 12/1990 | Ewall |
| 4,985,277 A | 1/1991 | Shimizu |
| 4,995,382 A | 2/1991 | Lang |
| 5,009,652 A | 4/1991 | Morgan |
| 5,074,944 A | 12/1991 | Trenka |
| 5,088,483 A | 2/1992 | Heinecke |
| 5,340,363 A | 8/1994 | Fabo |
| 5,395,305 A | 3/1995 | Koide |
| 5,409,472 A | 4/1995 | Rawlings |
| 5,445,604 A | 8/1995 | Lang |
| 5,512,041 A | 4/1996 | Bogart |
| 5,540,922 A | 7/1996 | Fabo |
| 5,635,201 A | 6/1997 | Fabo |
| 5,636,643 A | 6/1997 | Argenta |
| 5,782,787 A | 7/1998 | Webster |
| 5,981,822 A | 11/1999 | Addison |
| 6,040,492 A | 3/2000 | Lindquist |
| 6,051,747 A | 4/2000 | Lindqvist |
| 6,103,369 A | 8/2000 | Lucast |
| 6,194,332 B1 | 2/2001 | Rock |
| 6,584,668 B2 | 7/2003 | Green |
| 6,821,936 B2 | 11/2004 | Green |
| 6,946,433 B2 | 9/2005 | Green |
| 7,396,975 B2 * | 7/2008 | Sigurjonsson .......... A61L 15/58 |
| | | 602/41 |
| 7,468,471 B2 | 12/2008 | Sigurjonsson |
| 7,842,306 B2 | 11/2010 | Canada |
| 8,247,635 B2 | 8/2012 | Sigurjonsson |
| 2004/0001880 A1 | 1/2004 | Bowler |
| 2005/0037680 A1 * | 2/2005 | Canada ................... A61L 15/46 |
| | | 442/59 |
| 2005/0226914 A1 * | 10/2005 | Cottrell .................. A01N 59/16 |
| | | 424/443 |
| 2006/0079640 A1 * | 4/2006 | Ishii ..................... A61K 31/485 |
| | | 525/88 |
| 2006/0127462 A1 | 6/2006 | Canada |
| 2011/0208101 A1 | 8/2011 | Keller |
| 2019/0000677 A1 * | 1/2019 | Munro ............. A61F 13/00063 |

FOREIGN PATENT DOCUMENTS

| | | |
|---|---|---|
| WO | 2012028842 | 3/2012 |
| WO | 2012104584 | 8/2012 |
| WO | 2016109418 A1 | 7/2016 |
| WO | 2017115146 A1 | 7/2017 |
| WO | WO-2019027809 A1 * | 2/2019 ......... A61B 5/14539 |

* cited by examiner

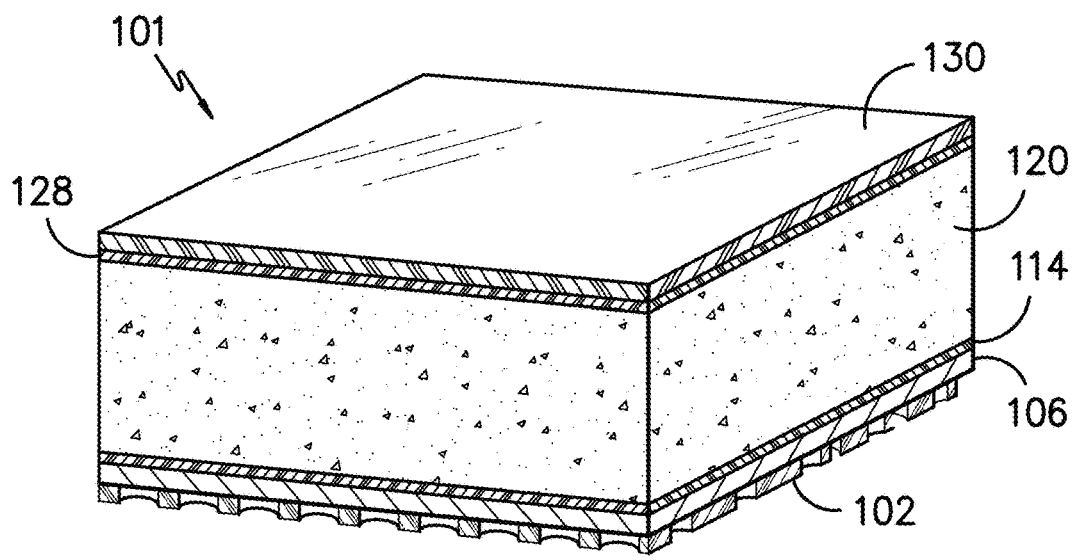
FIG. -1A-
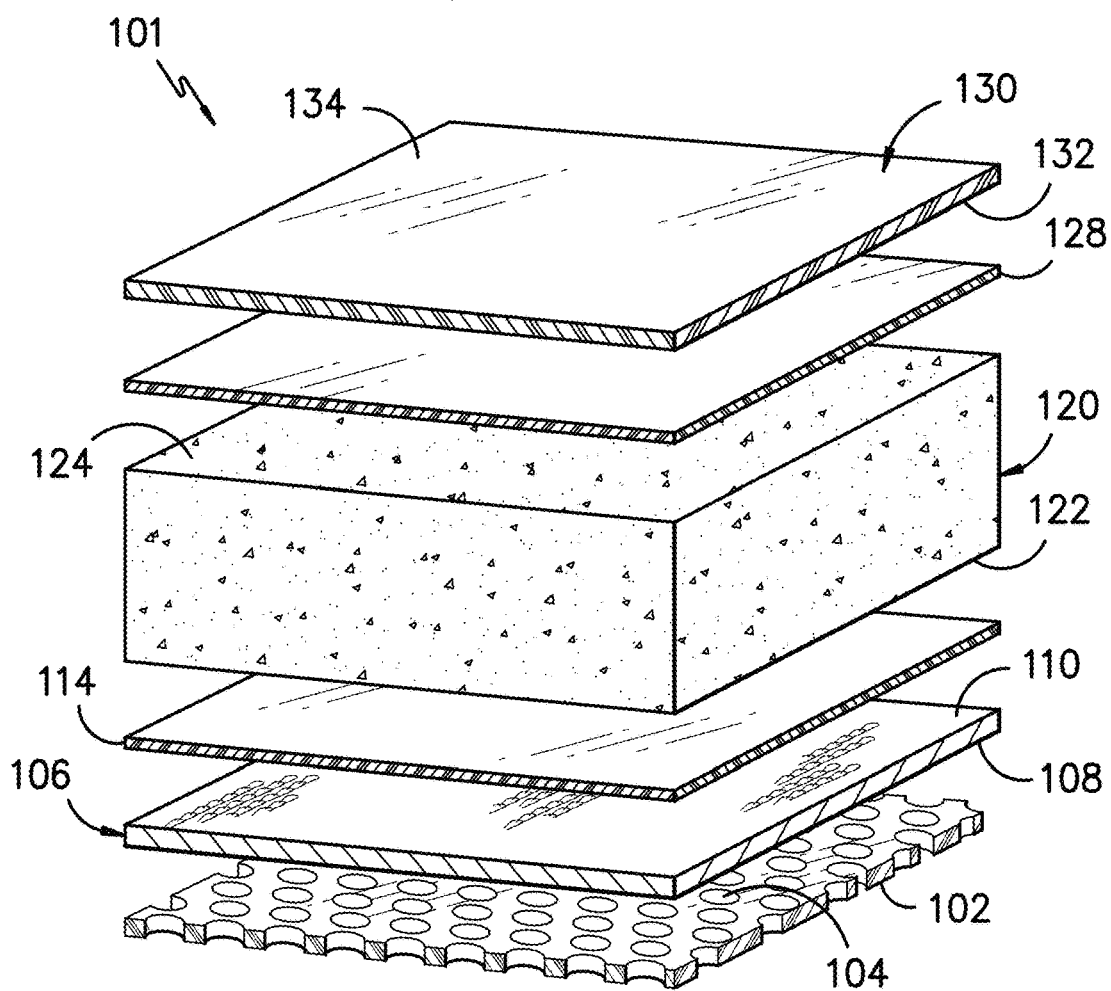
FIG. -1B-

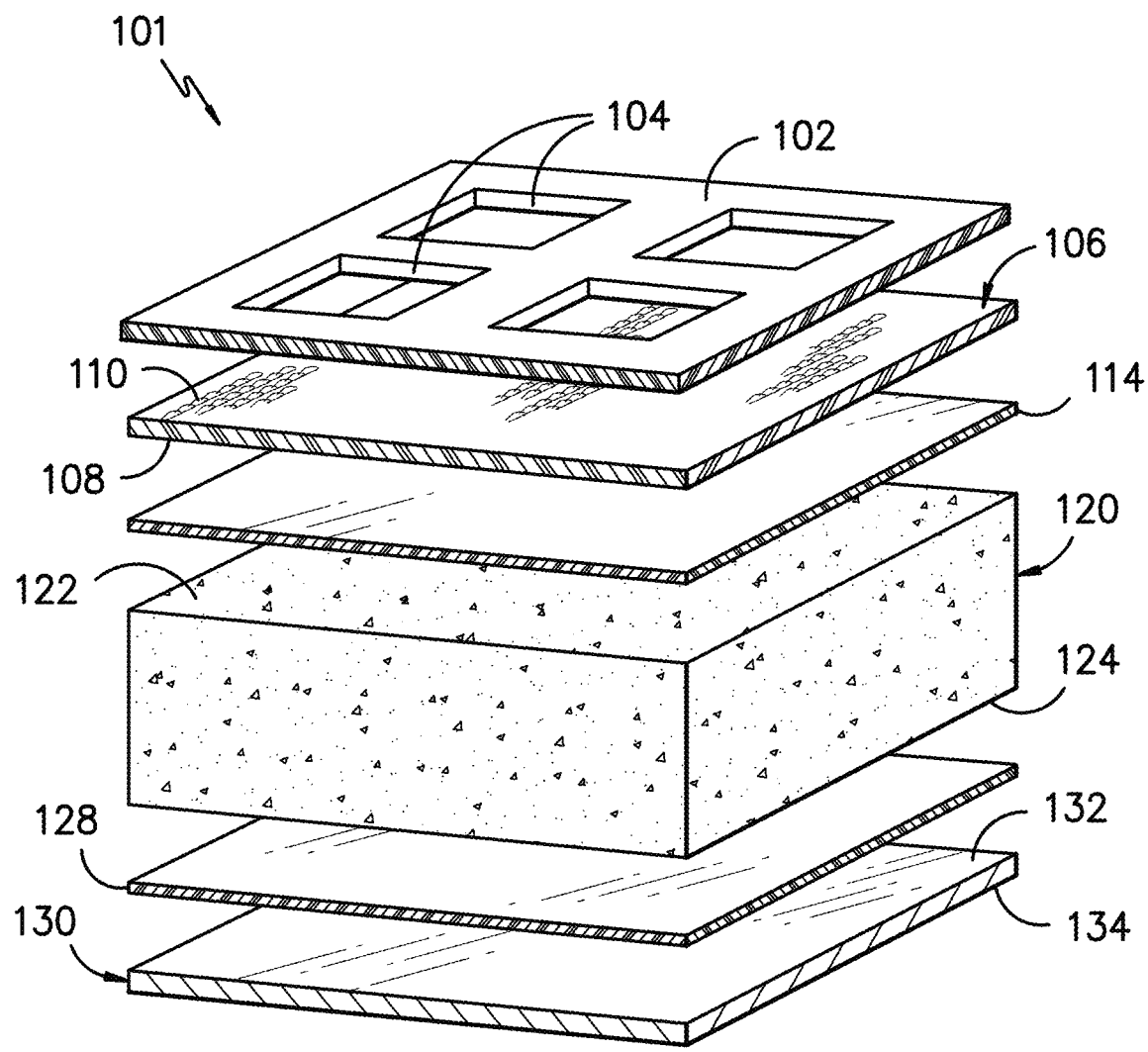
FIG. -1C-

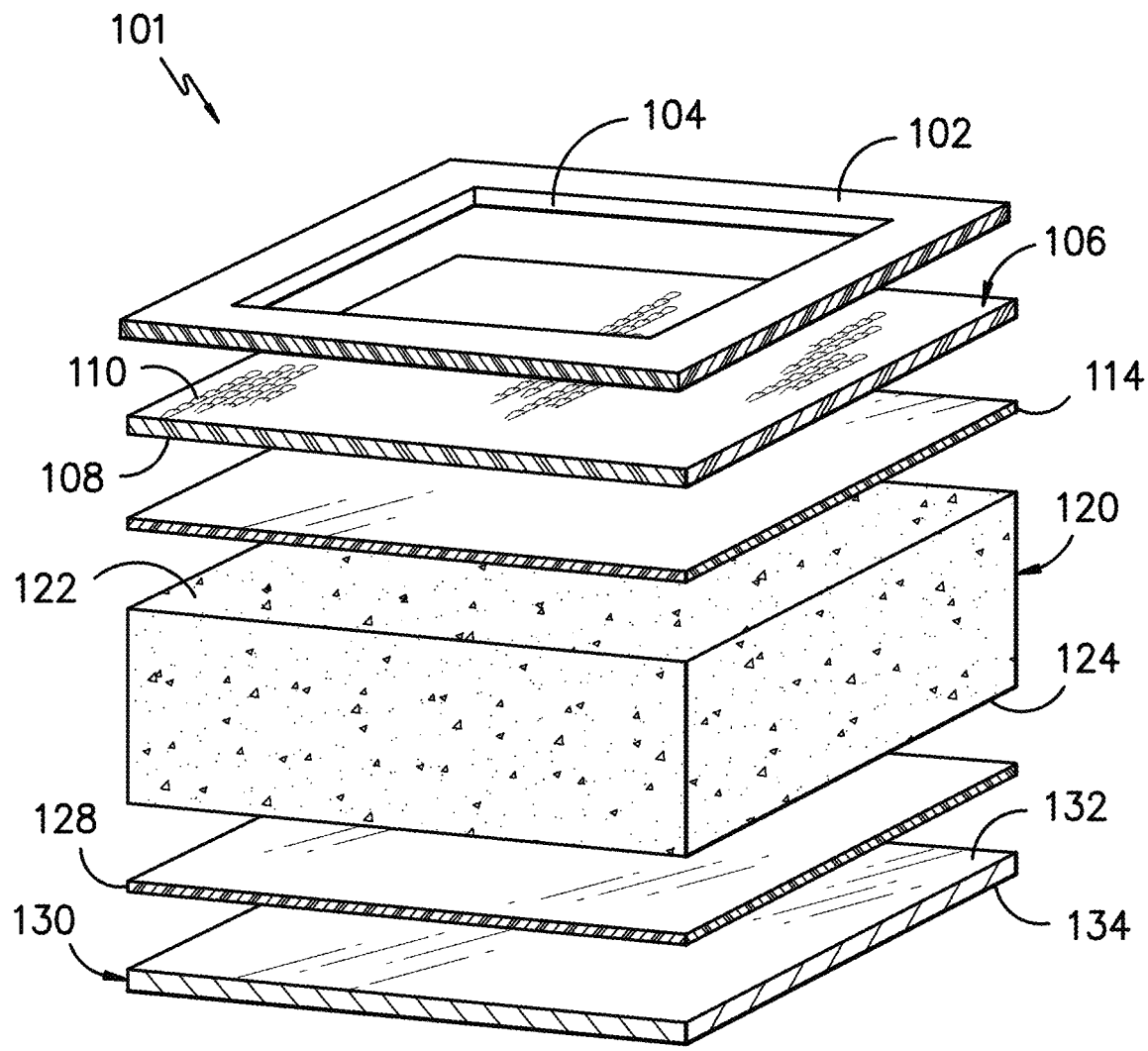
FIG. -1D-

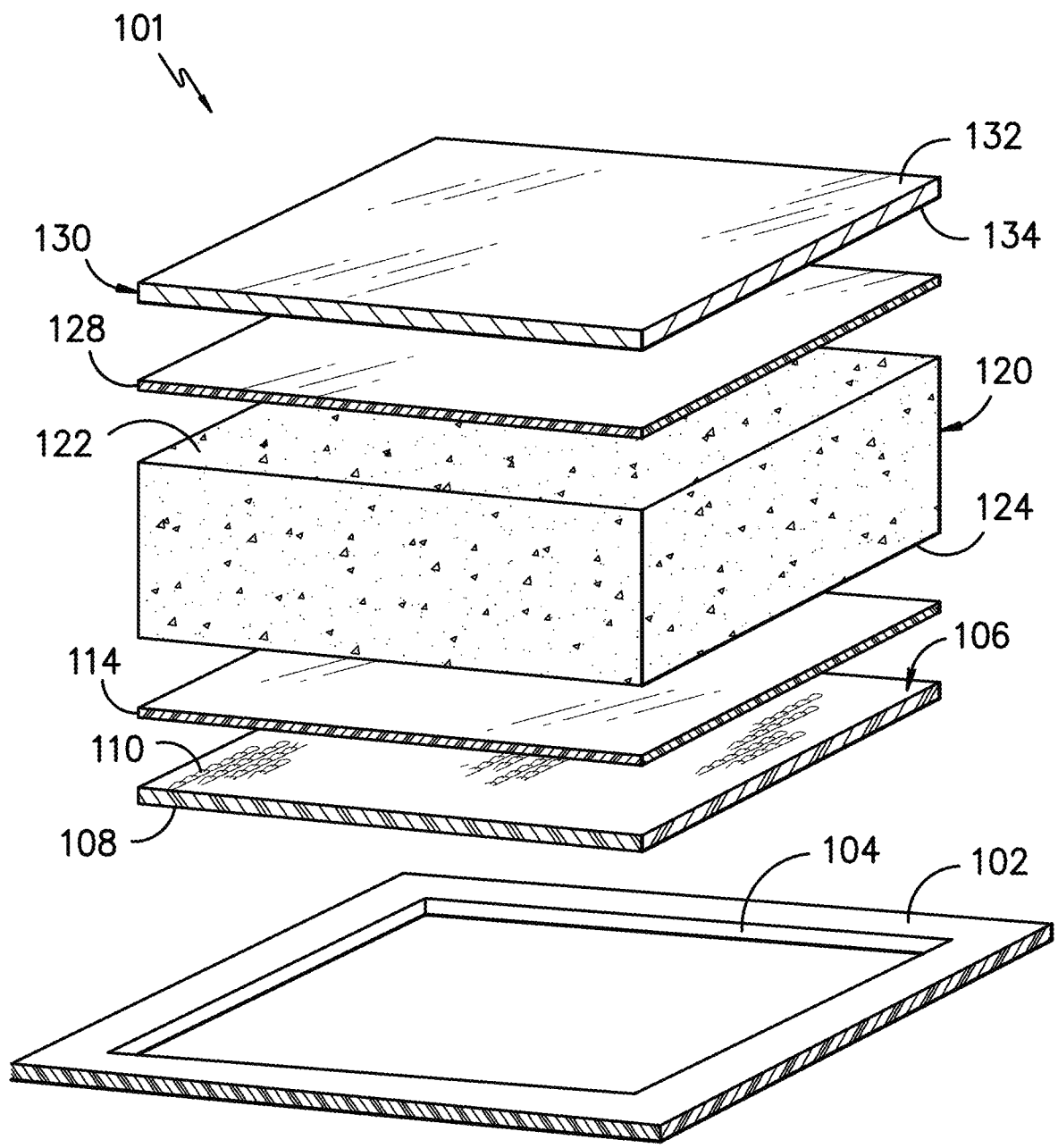
FIG. -1E-

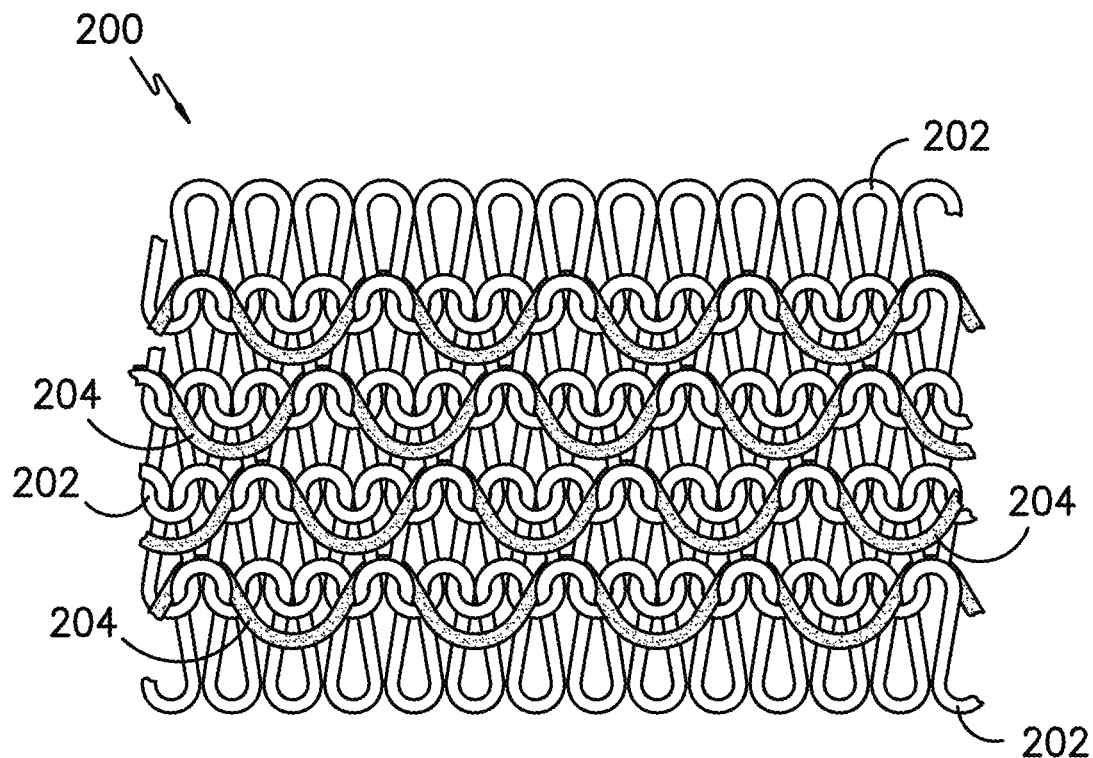
FIG. -2-
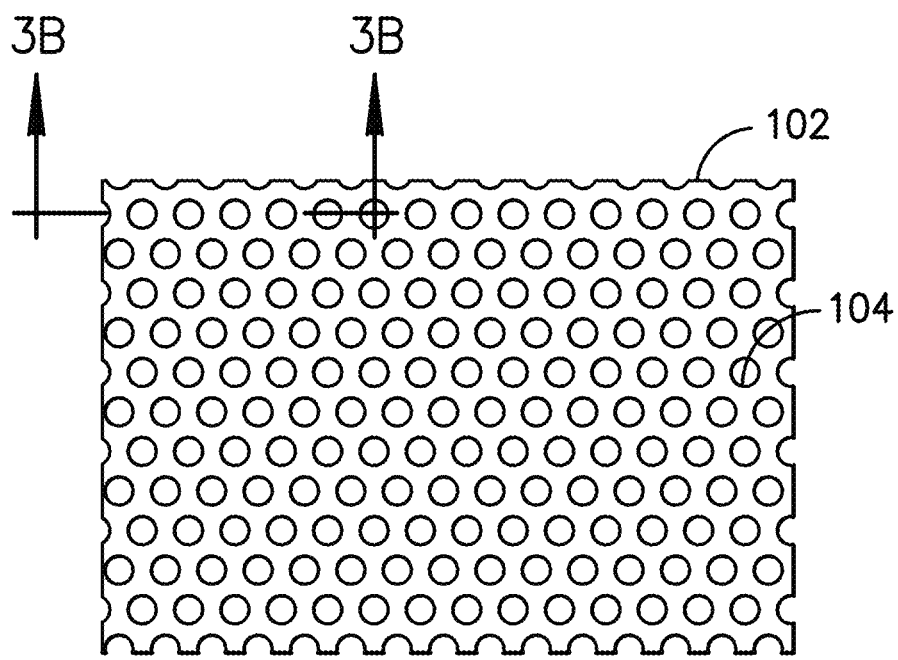
FIG. -3A-

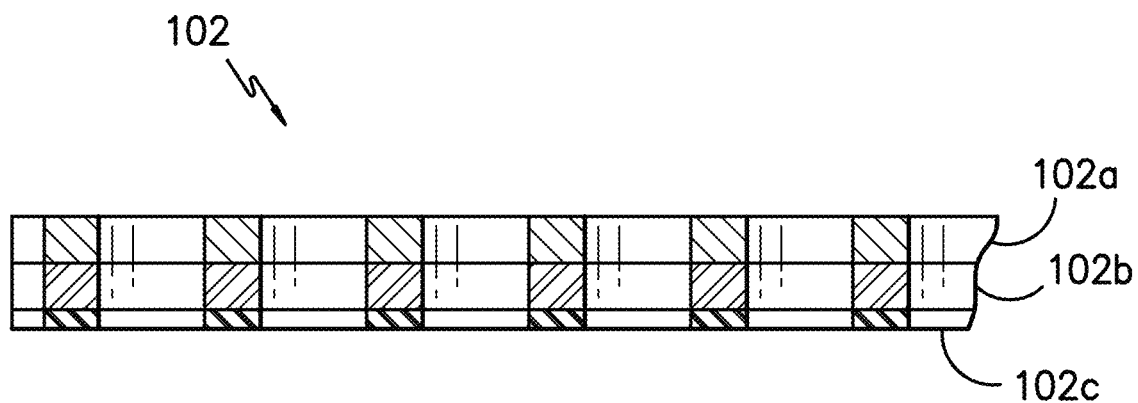
FIG. -3B-
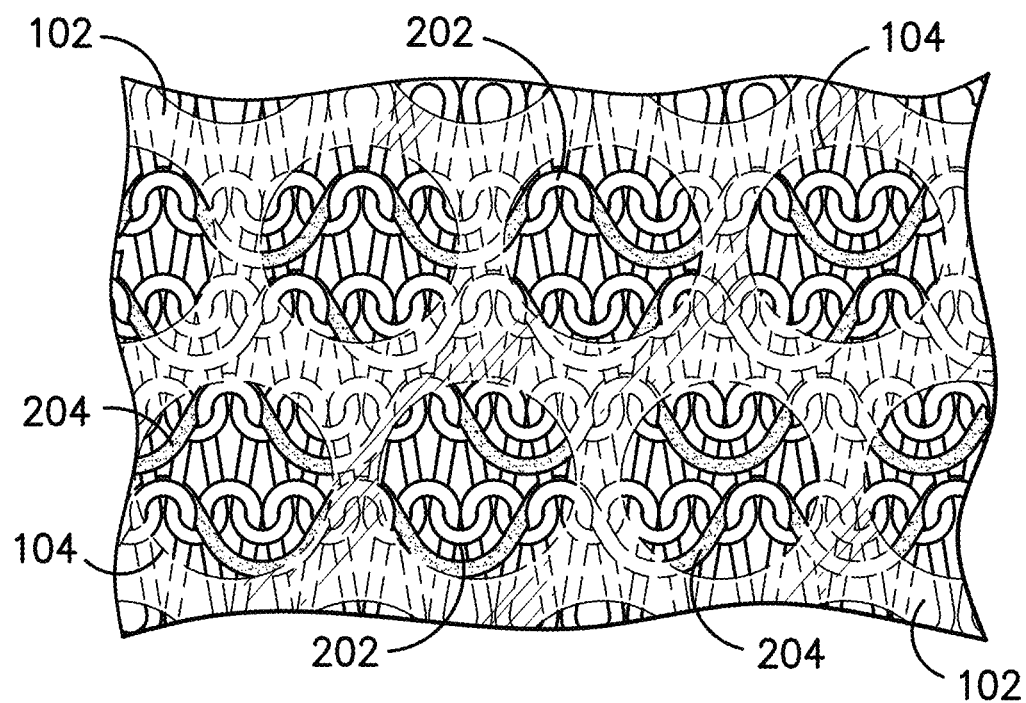
FIG. -4-

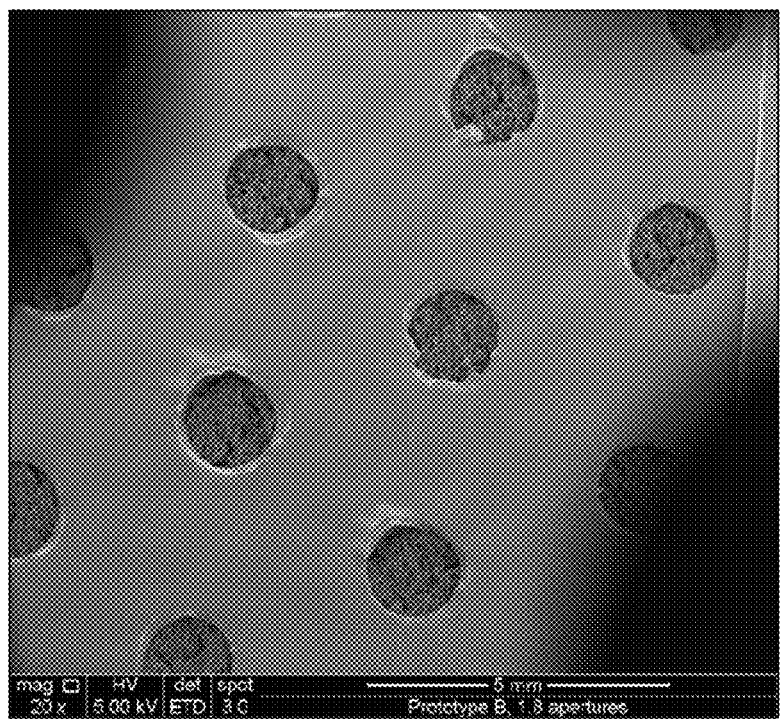
FIG. -5-
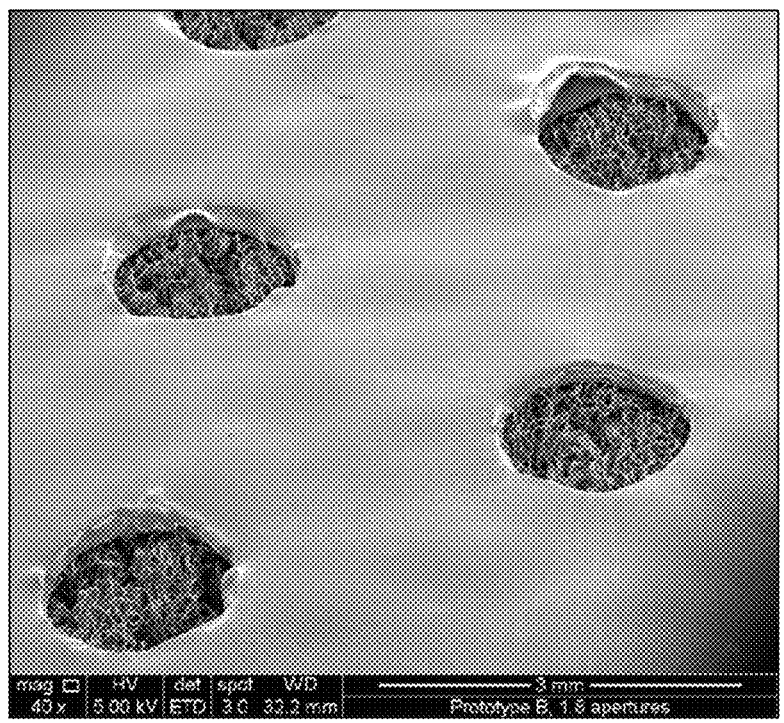
FIG. -6-

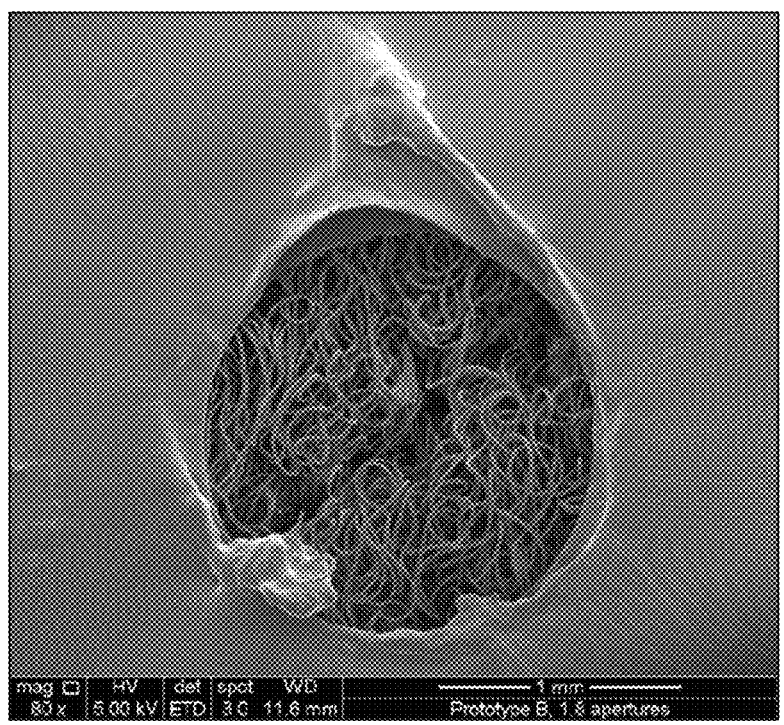
FIG. -7-
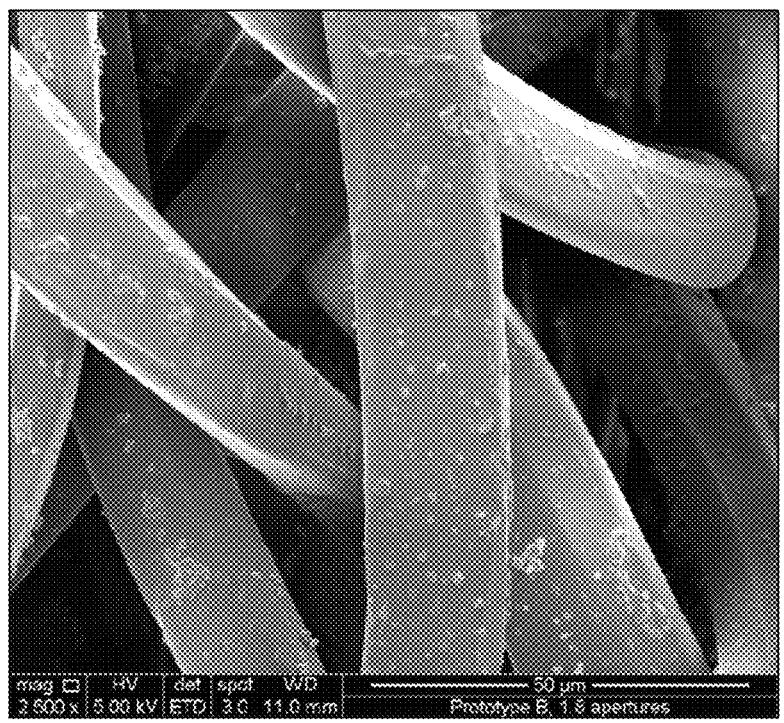
FIG. -8-

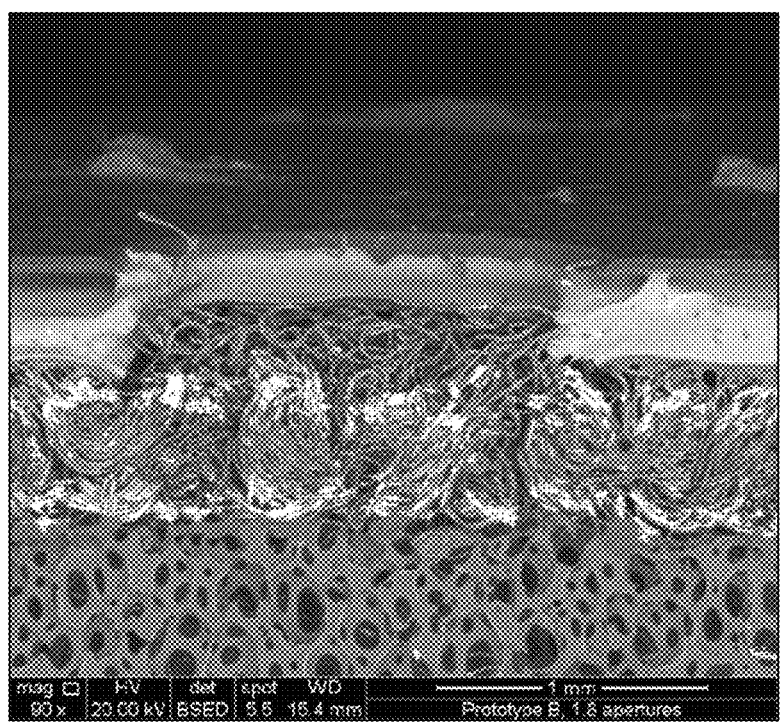
FIG. -9-
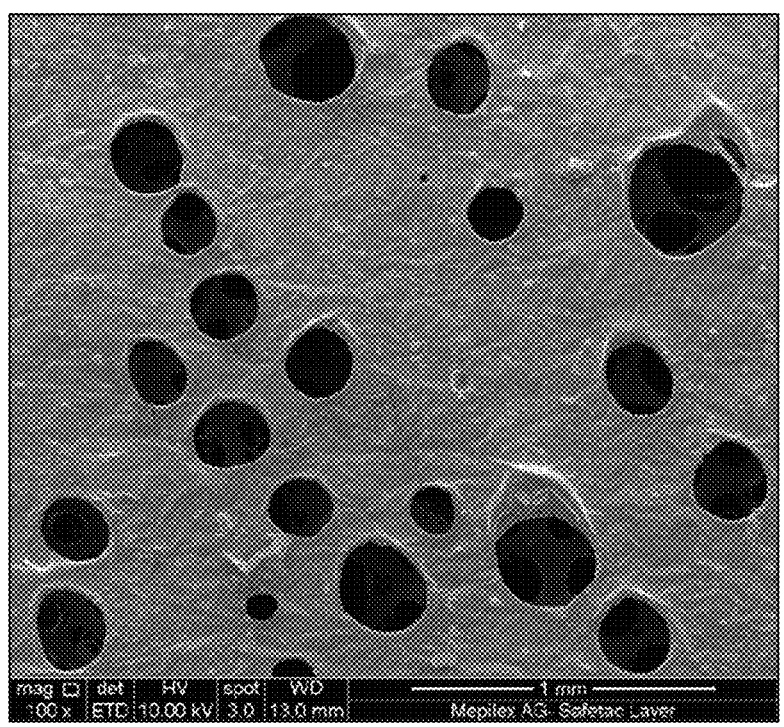
FIG. -10-

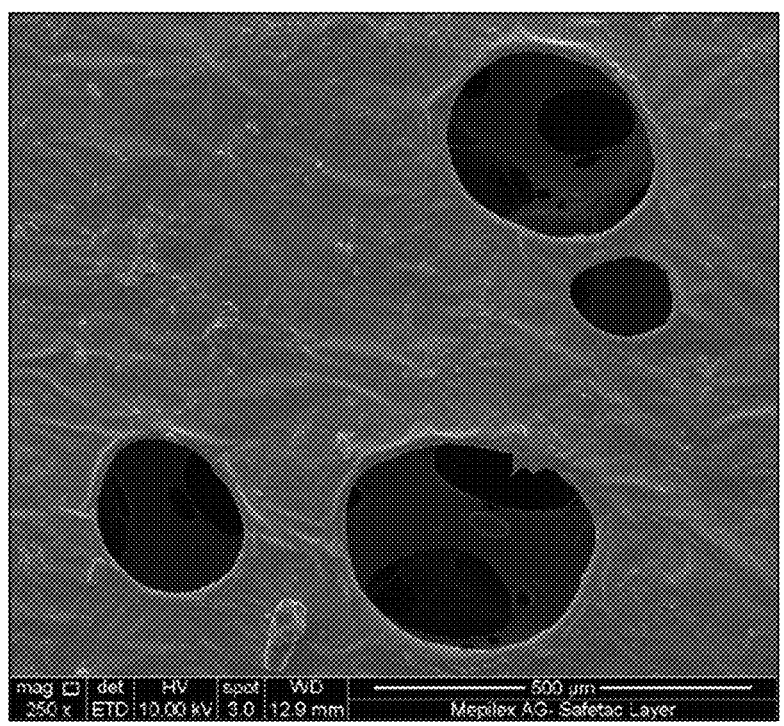
FIG. -11-
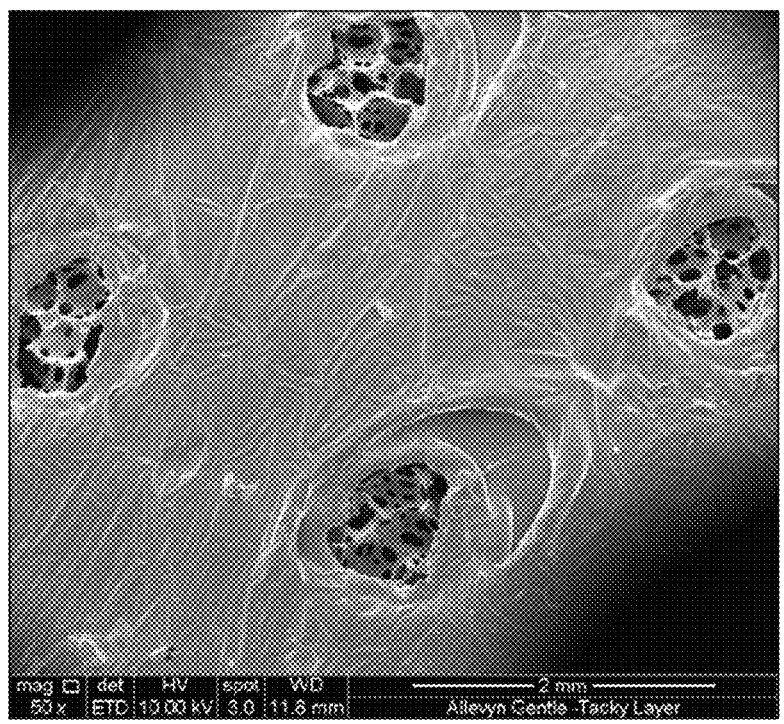
FIG. -12-

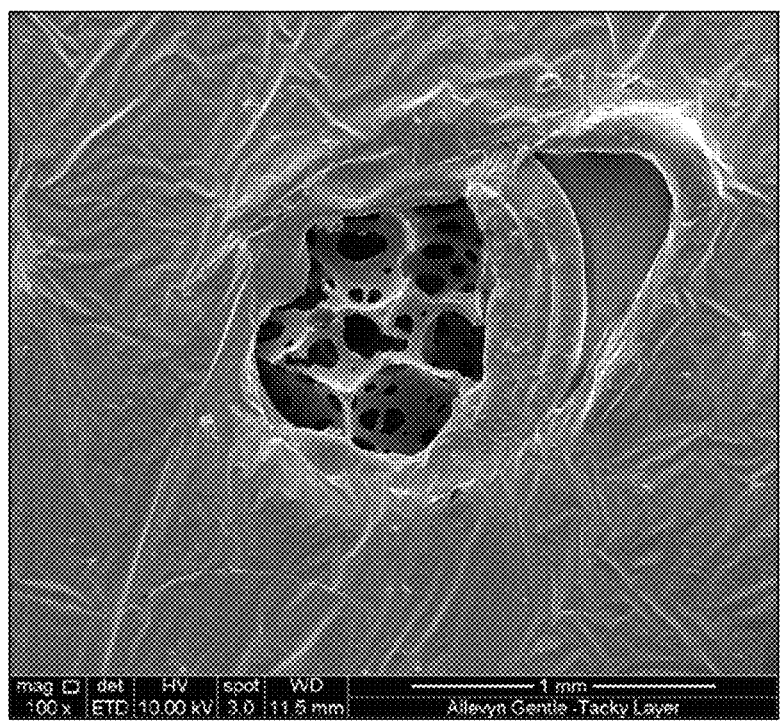
FIG. -13-

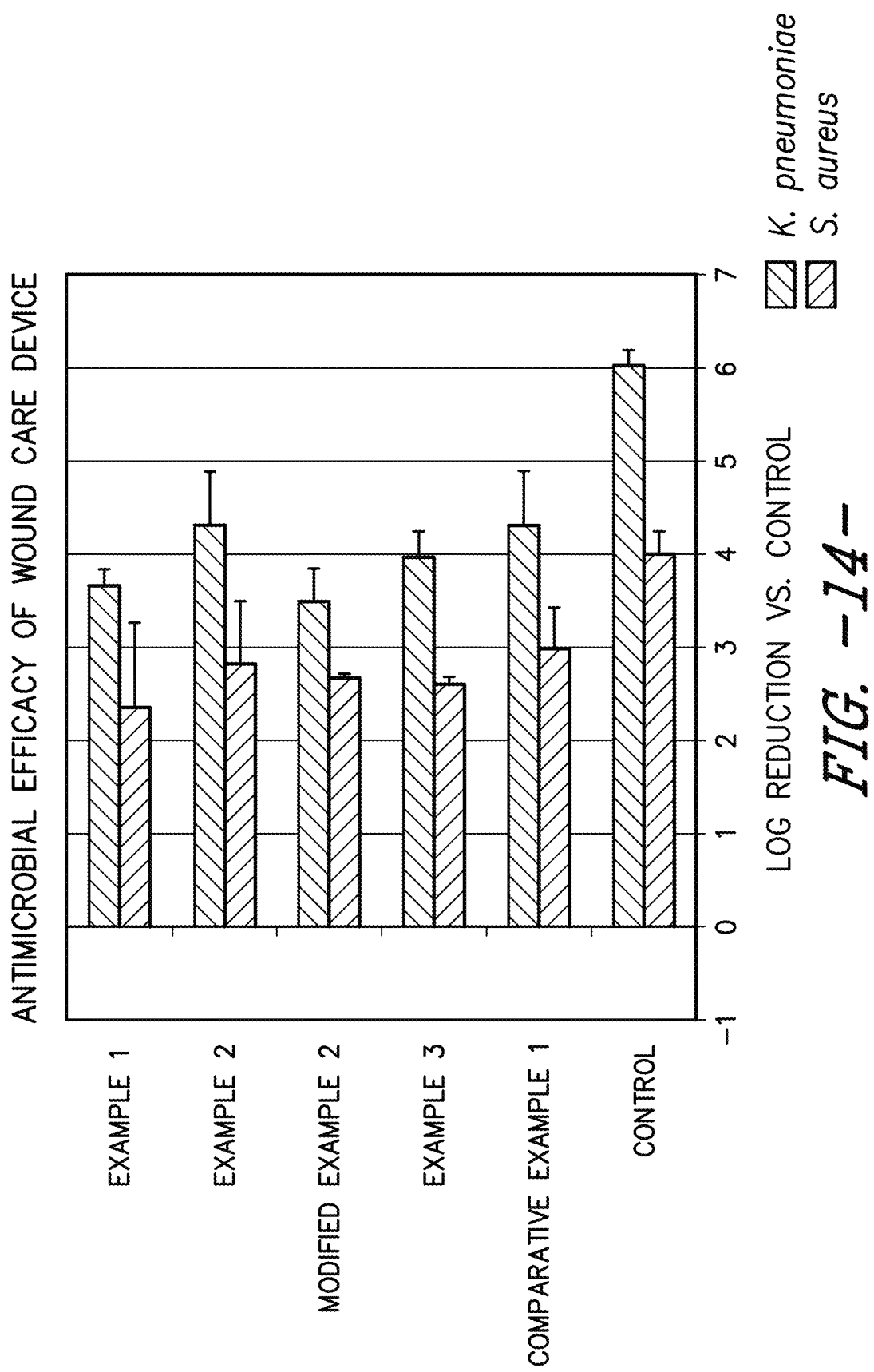
FIG. -14-

WOUND CARE DEVICE HAVING FLUID TRANSFER AND ADHESIVE PROPERTIES

CROSS REFERENCE TO RELATED APPLICATIONS

This application claims priority to and is a divisional of U.S. application Ser. No. 16/415,073, entitled "Wound Care Device Having Fluid Transfer and Adhesive Properties" which was filed on May 17, 2019, which claims priority to U.S. Provisional Patent Application No. 62/674,095, entitled "Wound Care Device Having Fluid Transfer and Adhesive Properties" which was filed on May 21, 2018, both of which are entirely incorporated by reference herein.

TECHNICAL FIELD

This disclosure relates to a wound care device which contains capillary force one-way pumps that are capable of transporting fluid, such as wound exudate, away from a wound site to the opposite side of the wound care device, which functions as a segregated fluid reservoir. This fluid transport mechanism generally aids in reducing wound maceration by removing excess wound fluid and the protease enzymes and infectious bacteria contained within the wound fluid. The wound care device performs this function, often times for multiple days, without the loss of the physical integrity of the wound care device. In addition to providing a uni-directional fluid transport mechanism, the wound care device contains a perforated adhesive layer.

In one aspect, the wound care device is comprised of a knit construction characterized in that polyester fiber is primarily present on the wound contact surface and nylon fiber is primarily present on the fluid reservoir surface. A third fiber, such as an elastomeric polyurethane known by the tradename Lycra®, may also be included in order to provide some amount of elasticity to the wound care device. The wound care device provides a one way directional flow of fluid away from the wound and into the nylon fluid reservoir. The perforated silicone gel adhesive layer, which is designed for direct contact with the wound, functions to prevent the wound care device from sticking to the wound.

BACKGROUND

In the medical field, and in the area of wound care particularly, it is well-established that many factors, including the amount of moisture present at a wound site, affects how quickly a wound will heal. Generally speaking, having an excessive amount of moisture present at a wound site, especially when combined with the warm environment provided by the body, leads to undesirable bacteria growth and production of protease enzymes in the wound. Such growth can cause further damage to healthy cells and delay the healing process. However, insufficient moisture at the wound site can cause eschar (scab) formation and scarring and may cause the wound care device, or medical dressing, to adhere to the wound. If the dressing adheres to the wound, subsequent removal of the dressing may cause undue discomfort to the patient as well as disrupt newly granulated tissue. Infection of the wound may also be compounded when a medical dressing is removed and portions of the dressing remain behind in the wound itself, particularly if the dressing is already colonized with pathogenic microbes. Thus, it is important that the dressing maintains its physical integrity when exposed to stress, such as during removal from the wound, in order to prevent additional complications and delays in healing.

Absorptive materials such as gauzes, hydrogels, swellable fibers, foams, woven textiles and the like have been incorporated into wound care devices for the purpose of controlling the wound moisture content. Fluids are generally absorbed by these types of materials by reversible capillary action or osmosis rather than by a one-way directional flow created by an inventive two-sided wound care device.

For example, U.S. Pat. No. 5,009,652 to Morgan et al. discloses a disposable laminated medical sponge that contains a thin film which is impervious to fluids and infectious agents. The medical sponge is designed to prevent the seepage of bodily fluids from one side of the sponge to the opposite side, since such seepage provides risk of infection for health-care workers having direct contact with patients.

U.S. Pat. No. 6,194,332 to Rock et al. discloses an antimicrobial composite fabric having a first inner fabric layer and a second outer fabric layer. The inner fabric layer may be comprised of polyester, acrylic or nylon fiber which has been rendered hydrophilic, such as by mechanical or chemical treatment. The hydrophilic inner fabric layer enables the transport of sweat from the inner fabric layer to the outer fabric layer. The fibers in the outer layer of the fabric may be blended with antimicrobial fibers in order to reduce the proliferation of bacteria in this layer. The fabric may be formed into a garment which provides reduced body odor. U.S. Pat. No. 6,602,811 to Rock et al. discloses a similar antimicrobial composite fabric, except that the second outer fabric layer also may be treated with an antimicrobial paste.

US Patent Application Publication No. 2004/0001880 to Bowler et al. discloses the use of gel forming fibers such as sodium carboxymethycellulose which can be incorporated into wound dressings. Silver ions may be incorporated into the fibers by combining them in a solution with a solvent prior to fiber formation. The dressing may be used as part of a larger dressing or a layer in a multi-layered dressing and need not be in direct contact with the wound.

The wound care device of the present invention takes advantage of a unique textile fabric construction which effectively isolates fluid away from the wound, along with a silicone gel adhesive layer which aids in preventing the wound care device from detrimentally sticking to the wound. Both of these features promote and improve the healing process. The differentiation that exists in a wound care device having a hydrophobic fiber on the wound contact side of the device and hydrophilic fiber on the fluid reservoir side of the device creates a unique one-way, directional flow of fluid and contaminants away from the wound.

A further feature of the wound care device of the present invention is that the device may also contain a topical coating of an antimicrobial agent such as silver. It is known that placing surface-available silver in contact with a wound allows the silver to enter the wound and become absorbed by undesirable bacteria and fungi that grow and prosper in the warm, moist environment of the wound site. Once absorbed, the silver ions kill microbes, resulting in treatment of infected wounds or the prevention of infection in at-risk wounds. Methods of topically applying a silver-based antimicrobial finish to textile substrates are described, for example, in commonly assigned U.S. Pat. Nos. 6,584,668; 6,821,936; and 6,946,433 and in commonly assigned U.S. patent application Ser. Nos. 09/586,081; 09/589,179; 10/307,027; and 10/306,968. All of these patents and patent applications are hereby incorporated by reference. Details of many of these processes will be discussed below.

The present disclosure addresses and overcomes the problems described above. Whereas, historically, a gauze or foam medical dressing has been applied to a wound with at least some intent on absorbing fluids, the present disclosure describes a wound care device capable of creating a one-way, directional flow of fluid and contaminants away from the wound, without detrimentally causing excessive dryness of the wound and substantial adherence of the device to the wound. The wound care device may additionally provide desired release of silver to the wound site for antimicrobial efficacy and, because of its unique construction, maintains its physical integrity when exposed to stress during ordinary use of the wound care device.

For these reasons and others that will be described herein, the present wound care device having unique fluid management properties and easy release/removal from the wound represents a useful advance over the prior art.

BRIEF SUMMARY

In one aspect, the invention relates to a wound care device comprising: a perforated trilaminate silicone adhesive layer; a single layer of fabric having a wound contact surface and a wound fluid reservoir surface; a fluid retentive layer; and wherein said wound care device transports wound fluid uni-directionally from said wound contact surface to said wound fluid reservoir surface upon exposure to a wound.

In another aspect, the invention relates to a wound care device comprising: (a) a perforated trilaminate silicone adhesive layer; (b) a single layer of fabric having a wound contact surface and a wound fluid reservoir surface; (c) optionally, a first hot melt adhesive layer; (d) a fluid retentive layer; (e) optionally, a second hot melt adhesive layer; (f) optionally, an occlusive film layer; and wherein said wound care device transports wound fluid uni-directionally from said wound contact surface to said wound fluid reservoir surface upon exposure to a wound.

In a further aspect, the invention relates to a method for managing moisture at a wound site comprising the steps of: (a) providing a wound care device comprising: (i) a perforated trilaminate silicone adhesive layer; (ii) a single layer of fabric having a wound contact surface and a wound fluid reservoir surface; and (iii) a fluid retentive layer; and wherein said wound care device transports wound fluid uni-directionally from said wound contact surface to said wound fluid reservoir surface upon exposure to a wound; (b) placing said wound contact surface of said wound care device in contact with said wound site; and (c) allowing said wound care device to transport wound fluid uni-directionally from said wound contact surface to said wound fluid reservoir surface.

In another aspect, the invention relates to a wound care device comprising: (a) a perforated trilaminate silicone adhesive layer; (b) a single layer of fabric having a wound facing surface and a wound fluid reservoir surface; and (c) a fluid retentive layer; and wherein said wound care device transports wound fluid uni-directionally from said wound facing surface to said wound fluid reservoir surface upon exposure to a wound.

BRIEF DESCRIPTION OF THE DRAWINGS

FIG. 1A is a perspective view of a wound care device according to the invention having a fluid transport layer and an apertured adhesive layer.

FIG. 1B is an exploded perspective view of the wound care device depicted in FIG. 1A.

FIG. 1C is a perspective view of a wound care device according to the invention having a fluid transport layer and an alternative apertured adhesive layer.

FIG. 1D is a perspective view of a wound care device according to the invention having a fluid transport layer and a border adhesive layer.

FIG. 1E is a perspective view of another embodiment of a wound care device according to the invention having a fluid transport layer and a border adhesive layer and further illustrating the adhesive layer extending beyond the other layers of the device.

FIG. 2 is a plan view of a laid-in fabric suitable for use as the fluid transport layer of a wound care device according to the invention.

FIG. 3A is a plan view of an apertured polymeric film, such as that depicted in FIGS. 1A and 1B, suitable for use as the adhesive layer of a wound care device according to the invention.

FIG. 3B is a side view of a trilaminate apertured polymeric film suitable for use as the adhesive layer of a wound care device according to the invention.

FIG. 4 is a plan view of a composite article according to the invention showing the surface of the composite article having the adhesive layer and the underlying fluid transport layer.

FIG. 5 is a photomicrograph at 20× magnification illustrating multiple apertures in the adhesive layer of the wound care device and the presence of fibers from the fluid transport layer being present in those apertures according to the invention.

FIG. 6 is a photomicrograph at 40× magnification illustrating multiple apertures in the adhesive layer of the wound care device and the presence of fibers from the fluid transport layer being present in those apertures according to the invention.

FIG. 7 is a photomicrograph at 80× magnification illustrating a single aperture in the adhesive layer of the wound care device and the presence of fibers from the fluid transport layer being present in the aperture according to the invention.

FIG. 8 is a photomicrograph at 2500× magnification illustrating the presence of silver-containing compounds on the fibers of the fluid transport layer according to the invention.

FIG. 9 is a photomicrograph at 90× magnification of a side view of a portion of the wound care device according to the invention.

FIG. 10 is a photomicrograph at 100× magnification illustrating the apertures in the adhesive layer of Comparative Example 1.

FIG. 11 is a photomicrograph at 250× magnification illustrating the apertures in the adhesive layer of Comparative Example 1.

FIG. 12 is a photomicrograph at 50× magnification illustrating the apertures in the adhesive layer of Comparative Example 3.

FIG. 13 is a photomicrograph at 100× magnification illustrating a single aperture in the adhesive layer of Comparative Example 3.

FIG. 14 is a bar graph illustrating antimicrobial efficacy of wound care devices of the present invention and Comparative Example 1.

DETAILED DESCRIPTION

Definitions and Terms

"Hydrophilic" is defined as having a strong affinity for or the ability to absorb water.

"Hydrophobic" is defined as lacking affinity for or the ability to absorb water.

"Non-electrically conductive" is defined as having a resistance in ohms per square inch of fabric of greater than about 10,000 ohms, preferably greater than about 100,000 ohms and most preferably greater than about $1\times10^9$ ohms, when measured in accordance with AATCC Test Method 76-1978.

As utilized herein, the term "surface energy" refers to the excess energy at the surface of a material compared to the bulk of the material (e.g., the interior portions of the material) and is usually expressed in terms of milliJoules per square meter ($mJ/m^2$). The surface energy quantifies the disruption of intermolecular bonds that occurs when a surface is created. The surface energy can be measured by several means including, for example, the Fowkes method. In this method, two reference liquids are used to first measure the dispersive component and the polar component of the material's surface energy. The surface energy of the material is then calculated from the measured dispersive and polar components. In general, a surface having a higher surface energy will exhibit a higher affinity for aqueous fluids, such as perspiration or wound exudate.

Wound Care Device

The wound care device of the present invention is generally intended to be used for treatment of various wounds including, without limitation, partial thickness burns, incisions, skin grafts, donor sites, lacerations, abrasions, Stage I-IV pressure ulcers, vascular venous stasis, and diabetic ulcers. The wound care device is generally comprised of: (a) a layer of fabric formed from synthetic fibers, natural fibers, or combinations thereof, and (b) a layer of perforated silicone gel adhesive.

Synthetic fibers comprising the fabric layer include, for example, polyester, acrylic, polyamide, polyolefin, polyaramid, polyurethane, regenerated cellulose (i.e., rayon), and blends thereof. The term "polyamide" is intended to describe any long-chain polymer having recurring amide groups (—NH—CO—) as an integral part of the polymer chain. Examples of polyamides include nylon 6; nylon 6, 6; nylon 1, 1; and nylon 6, 10. The term "polyester" is intended to describe any long-chain polymer having recurring ester groups (—C(O)—O—). Examples of polyesters include aromatic polyesters, such as polyethylene terephthalate (PET), polybutylene terephthalate (PBT), polytrimethylene terephthalate (PTT), and polytriphenylene terephthalate, and aliphatic polyesters, such as polylactic acid (PLA). "Polyolefin" includes, for example, polypropylene, polyethylene, and combinations thereof. "Polyaramid" includes, for example, poly-p-phenyleneteraphthalamid (i.e., Kevlar®), poly-m-phenyleneteraphthalamid (i.e., Nomex®), and combinations thereof. Natural fibers include, for example, wool, cotton, flax, and blends thereof.

The fabric may be formed from fibers or yarns of any size, including microdenier fibers and yarns (fibers or yarns having less than one denier per filament). The fibers or yarns may have deniers that range from less than about 1 denier per filament to about 2000 denier per filament or more preferably, from less than about 1 denier per filament to about 500 denier per filament, or even more preferably, from less than about 1 denier per filament to about 300 denier per filament.

Furthermore, the fabric may be partially or wholly comprised of multi-component or bi-component fibers or yarns, which may be splittable, or which have been partially or fully split, along their length by chemical or mechanical action. The fabric may be comprised of fibers such as staple fiber, filament fiber, spun fiber, or combinations thereof.

The fabric may be of any variety, including but not limited to, woven fabric, knitted fabric, nonwoven fabric, or combinations thereof. The fabric may optionally be colored by a variety of dyeing techniques, such as high temperature jet dyeing with disperse dyes, vat dyeing, thermosol dyeing, pad dyeing, transfer printing, screen printing, or any other technique that is common in the art for comparable textile products. If yarns or fibers are treated by the process of the current invention, they may be dyed by suitable methods prior to fabric formation, such as, for instance, by package dyeing or solution dyeing, or after fabric formation as described above, or they may be left undyed.

Other additives may be present on and/or within the target fabric or yarn, including antistatic agents, optical brightening compounds, opacifiers (such as titanium dioxide), nucleating agents, antioxidants, UV stabilizers, fillers, permanent press finishes, softeners, lubricants, curing accelerators, adhesives, and the like. The present fabrics may also be coated or printed or otherwise aesthetically modified in addition to being treated with the present antimicrobial compositions. Printing may be achieved, for example, by screenprinting or flexographic printing techniques.

One specific example of a knit pattern that is suitable for making the fabric that comprises the wound care device of the present invention is a jersey knit. A jersey knit is a circular or flat-knit fabric made with a plain stitch in which the loops intermesh in only one direction. As a result, the appearance of the face and the back of the jersey fabric is wholly different. Thus, by utilizing a jersey knit to form a fabric comprised of polyester, nylon, and elastomeric fibers, a fabric may be constructed that is primarily polyester-containing on one side while the opposite side of the fabric is primarily nylon-containing. The elastomeric fiber provides some level of stretch to the fabric, which may be useful for some wounds that require, for example, a dressing to be wrapped snugly around the wound site. The elastomeric fiber, in addition to providing conformability to the wound care device, also provides some level of softness to the device. Spandex is one non-limiting example of an elastomeric fiber and may be known by the tradename Lycra®, which is available from INVISTA of Wichita, Kansas.

Additionally, it may be generally known to those skilled in the art that a knit polyester fabric tends to be hydrophobic, slow to absorb liquids, and generally exhibits little or no wicking of moisture. Since polyester is hydrophobic in nature, conventional wisdom would lead one to choose a hydrophilic natural fiber, such as cotton, or a hydrophilic synthetic fiber, such as nylon, as the wound contacting side of the wound care device. However, it was unexpectedly discovered that by placing a hydrophobic polyester containing surface against the wound site and a hydrophilic nylon containing surface away from the wound site, a unique one-way, directional flow of fluid away from the wound site was achieved.

As noted above, the fluid transport layer 106 comprises a first surface 108 and a second surface 110. The first surface 108 of the fluid transport layer 106 has a first surface energy, and the second surface 110 of the fluid transport layer 106 has a second surface energy. In one embodiment, the surface energy of the second surface 110 of the fluid transport layer 106 is greater than the surface energy of the first surface 108 of the fluid transport layer 106. This difference in surface energies between the two surfaces means that the second surface 110 of the fluid transport layer 106 exhibits a greater affinity for aqueous fluids (e.g., perspiration or wound exudates) than the first surface 108 of the fluid transport layer 106. Thus, any aqueous fluids absorbed by the fluid transport layer 106 will be transported or pumped from the first surface 108 to the second surface 110 of the fluid transport layer 106. This active transportation or pumping of the fluids ensures that excess moisture does not accumulate at the interface of fluid transport layer 106 and a fluid exuding surface, such as the skin or an exuding wound.

When the fluid transport layer comprises first and second surfaces having different surface energies, the difference between the two surface energies can be of any suitable magnitude. In a specific embodiment, the surface energy of the second surface 110 of the fluid transport layer 106 can be about 101% or more of the surface energy of the first surface 108 of the fluid transport layer 106. In more specific embodiments, the surface energy of the second surface 110 can be about 102% or more, about 103% or more, or about 104% or more of the surface energy of the first surface 108.

In a specific embodiment, the fluid transport layer 106 can be a textile material in which the surface energy of the second surface 110 is higher than the surface energy of the first surface 108. In order to provide the differential surface energies described above, the fluid transport layer can also comprise a material in which one surface has been chemically or physically modified to yield a material having first and second surfaces exhibiting different surface energies. For example, in one embodiment, the fluid transport layer can be a textile material such as those described above having a first surface that has been chemically treated in order to lower the surface energy thereof. In such an embodiment, the textile material can be treated, for example, with a relatively hydrophobic fluorocarbon or silicone (i.e., a fluorocarbon or silicone that is more hydrophobic than the material comprising the non-treated side of the textile material).

As shown in FIG. 2, such a construction results in a fabric in which the technical face of the fabric is predominantly one type of yarn 202, and the technical back presents a higher proportion of the effect yarn(s) 204. Thus, when the yarn 202 and the effect yarn 204 have different surface energies or one is more hydrophilic than the other, the resulting fabric will exhibit a different surface energy on each of the two major surfaces. In a specific embodiment of the fluid transport layer depicted in FIG. 2, the yarn(s) 202 are more hydrophilic than the effect yarn(s) 204. For example, the yarn(s) 202 can be polyamide yarns (e.g., nylon yarns), and the effect yarn(s) 204 can be polyester yarns. Such an embodiment of the fluid transport layer provides a layer in which the technical face of the fabric exhibits a higher surface energy than the technical back of the fabric. Thus, when utilized as the fluid transport layer of the composite article depicted in FIGS. 1A to 1E, such a fabric (i.e., the fabric depicted in FIG. 2) is disposed so that the technical back of the fabric forms the first surface 108 of the fluid transport layer 106 and the technical face of the fabric forms the second surface 110 of the fluid transport layer 106.

While fiber types are known to be generally hydrophilic or hydrophobic in their natural or initial manufactured condition, this condition can be changed with chemical and/or physical modification to the fibers and/or textile substrates containing the fibers. For instance, polyester fiber could be made to exhibit hydrophilic properties via chemical and/or mechanical treatment. Chemical treatments that may make normally hydrophobic fibers/fabrics more hydrophilic include, for example, Visa Endurance® fabric treatment available from Milliken & Company of Spartanburg, SC. Mechanical treatments that may make normally hydrophobic fibers/fabrics more hydrophilic include, for example, exposure to mechanical face finishing processes. Exemplary mechanical treatments include face finishing treatments like sanding, napping, calendaring, hydroentanglement with gas or liquid, and the like, and combinations thereof. As a result of these options, in one aspect of the invention, a suitable fabric may be comprised of treated polyester fiber exhibiting hydrophilic properties and treated polytetrafluoroethylene ("PTFE") fibers exhibiting hydrophobic properties. In another aspect, a suitable fabric may be comprised of fibers, such as cotton, viscose, or lyocell, with higher hydrophilicity than nylon and treated nylon fibers exhibiting hydrophobic properties.

The layer of perforated silicone gel adhesive is comprised of polydimethylsiloxane (also referred to herein as "PDMS" and/or "silicone") and its derivatives. In one aspect, the perforated silicone gel adhesive is comprised of multiple layers. For example, the perforated trilaminate silicone adhesive layer may be comprised of a skin facing silicone layer, a polyurethane layer (e.g. a polyurethane film), and an acrylic pressure sensitive adhesive layer. In another aspect of the invention, additional adhesive materials may be used in place of, or in combination with, the silicone gel adhesive. Therefore, the adhesive layer of the present invention may be comprised of materials selected from the group consisting of natural rubber-based adhesive materials, synthetic rubber-based adhesive materials, hydrocolloid materials, acrylate and/or acrylic materials, polyurethane gel materials, polydimethylsiloxane materials, and the like, and mixtures thereof. In addition, one or more of the following types of adhesive materials may be suitable for use as the adhesive layer of the wound care device of the present invention:

TABLE A

| Types of Adhesive Materials |
| --- |
| Ultraviolet and/or Visible Acrylics and/or Acrylates |
| Indigo Visible Acrylics and/or Acrylates |
| Flashcure Cyanoacrylates |
| Silicones |
| Cyanoacrylates |
| Polyurethane Gel |
| Polyurethane |
| Synthetic Rubber |
| Surface Insensitive |
| Low Odor and/or Low Bloom |
| Toughened and/or Flexible |
| General Purpose |
| Primers and/or Accelerators |
| One-Part Heat Cure Epoxies |
| Two-Part Room Temperature Cure Epoxies and/or Urethanes |
| Thermally Conductive Compound |
| Thermally Conductive Gel |

Accordingly, any of the foregoing adhesive materials and/or types of adhesive materials may be used alone, or in combination with one another, as the adhesive material comprising the adhesive layer of the wound care device of the present invention. It is also contemplated to be within the scope of the present invention that at least one antimicrobial agent may be included in the adhesive material comprising the adhesive layer.

The perforations in the adhesive layer may be of any shape and size suitable for the end-use application of the wound care device. In one aspect, a mechanical or electronic rotary die punch machine may be used to create the perforations in the adhesive layer. The perforations may be created in the adhesive layer prior to assembling the wound care device (e.g. a pre-perforated sheet of silicone), or the perforations may be added after at least part of the wound care device has been assembled. In the latter instance, a needle punching apparatus may be used to needle punch the fluid transport layer through the adhesive layer. This perforation method may create the apertures in the adhesive layer and cause the fibers of the fluid transport layer to be pulled through the apertures.

The apertures forming the perforations may be of any size. In one aspect, the apertures in the silicone layer are in the range from about 0.1 mm to about 7 mm, or in the range from about 1.0 mm to about 3.0 mm, or even in the range from about 1.3 mm to about 1.9 mm. The apertures may be present in the adhesive layer in any pattern. In one aspect, the distribution of apertures is present in a regular, uniform arrangement. In another aspect, the distribution of apertures may be present in the adhesive layer in a non-uniform arrangement.

In one aspect, the apertures in the adhesive silicone layer may be in the form of "windows" or openings that are larger in diameter than conventional apertures or small holes. In this regard, the apertured adhesive layer may include one window (or opening) or multiple windows (or openings) in the layer. These larger windows or openings may be present in a uniform or non-uniform pattern across the surface of the adhesive layer. When one large window is present in the approximate center of the apertured adhesive layer, the configuration may be referred to as a "border" adhesive since adhesive material is present only around the outer edges ("border") of the silicone adhesive layer. One advantage of these window and/or border adhesive layers is that the fluid transport layer, which is present immediately behind the adhesive layer, will have increased surface contact with the wound site. It is believed that having more wound contact may increase the ability of the fluid transport layer to absorb excessive fluid from the wound site and further promote wound healing. These window and border adhesive layers are further illustrated one or more of the Figures presented herein.

The percent of perforation (e.g. open space due to apertures or holes or openings) present in the perforated silicone gel adhesive layer may vary. In one aspect, the percent of perforation is in the range from about 5 percent to about 95 percent, or in the range from about 10 percent to about 40 percent, or even in the range from about 11 percent to about 20 percent.

The perforated silicone gel adhesive layer may be of any thickness. In one aspect, the perforated silicone gel adhesive layer has a thickness in the range from about 0.05 mm to about 1.0 mm, or in the range from about 0.1 mm to about 0.5 mm, or even in the range from about 0.2 mm to about 0.48 mm.

The adhesive characteristics of the silicone layer are fine-tuned and balanced to allow a minimum amount of adhesion to the skin and/or wound site for ease of application of the wound care device, but is contained and capped at a maximum amount of adhesion to prevent disruption of wound healing upon removal of the device from the wound. Without being bound by theory, it is believed that silicone is a preferably adhesive due to its high initial tack which can adhere to the skin for several days. However, the adhesive is gentle enough to not damage the wound or periwound skin upon removal. The adhesive characteristics may be measured by ASTM D6862-11, Standard Test Method for 90 Degree Peel Resistance of Adhesives. Ideal adhesion of the wound care device on a stainless steel substrate may be found in the range from about 0.1 N/25 mm to about 4.0 N/25 mm, or in the range from about 0.5 N/25 mm to about 2.0 N/25 mm.

Additional layers of material may be included with the wound care device of the present invention. For example, a fluid retentive layer may be attached to the fabric layer. The fluid retentive layer may be attached using hot melt adhesive. Also, an occlusive (non-perforated) film layer may be attached to the foam layer. The occlusive film layer may be attached using hot melt adhesive. Finally, a release liner may be included as part of the packaging of the wound care device. It functions to protect the silicone gel adhesive prior to use. The release liner is intended to be removed prior to use of the wound care device. The release liner may be comprised of material selected from the group consisting of polycarbonate, polypropylene, polyethylene, coated paper, and the like, and combinations thereof. The release liner may be printed.

The fluid retentive layer may be selected from the group consisting of foams, textile materials (e.g. woven, knit, and nonwoven textile materials), alginates, superabsorbent polymers, gels (e.g., hydrogels), and combinations or mixtures thereof. The fluid retentive layer can also comprise a combination of two or more discrete layers, which layers can comprise any of the absorptive materials listed above. In a specific embodiment, the fluid retentive layer can be a foam, such as an open cell, non-reticulated polymer foam. Such foams can be made from any suitable material including, but not limited to, polyurethane polymers. In one aspect, a polyurethane polymer used in making such a foam can be a polyester-based polyurethane polymer (i.e., a polyurethane polymer made from a reaction mixture containing a polyester polyol).

The fluid retentive layer of the wound care device may exhibit any suitable absorptive capacity. For example, the fluid retentive layer may exhibit a fluid absorption of about 100 wt % or more based on the weight of the fluid retentive layer. In a specific embodiment, the fluid retentive layer may exhibit a fluid absorption of about 200 wt % or more, about 300 wt % or more, about 400 wt % or more, about 500 wt % or more, about 600 wt % or more, about 700 wt % or more, about 800 wt % or more, about 900 wt % or more, or about 1000 wt % or more based on the weight of the fluid retentive layer. The absorptive capacity of the fluid retentive layer may be measured by any suitable means. For example, the absorptive capacity of the fluid retentive layer may be measured by immersing a known weight of the fluid retentive layer in phosphate-buffered saline containing 0.9 wt % sodium chloride at 37° C. for 30 minutes.

Thus, the wound care device of the present invention is comprised of a fabric layer and a perforated silicone gel adhesive layer. The wound care device may optionally include a release liner that is substantially coextensive with the silicone layer. The wound care device may also optionally include a fluid retentive layer that is attached to the fabric layer. The fluid retentive layer may or may not be substantially coextensive with the fabric layer. Another optional layer comprises an occlusive film layer. In one aspect, the occlusive film layer is substantially coextensive with the fluid retentive layer. The occlusive film layer may be printed with a product logo or other product identification information.

The wound care device of the present invention may be of any thickness, depending on the construction of the fabric and the thickness of the perforated silicone gel adhesive layer. In one aspect, the thickness of the wound care device may be in the range from about 25 to about 60 mils, or in the range from about 35 to about 50 mils, or even in the range from about 38 to about 45 mils. It should be understood, and is exemplified herein, that thickness measurements may be increased when the wound care device also includes an antimicrobial finish on one or more surfaces of the wound care device.

An additional advantageous feature of the silver-containing wound care device of the present invention is its ability to substantially maintain its original color, despite the presence of effective amounts of a silver-based antimicrobial agent. The elimination of color normally associated with the inclusion of silver-based antimicrobials is highly beneficial and desirable. The wound care devices (preferably, white-colored), as will be described herein, allow users thereof and their health care providers to monitor the exudates from the wound. Further, the present wound care devices exhibit long-term color stability (that is, their color does not change significantly over time while in production, transit, or storage). Finally, because the present wound care device is not discolored by the addition of the silver-based antimicrobial agent, a variety of substrate colors may be utilized or the finished wound care devices may be dyed or colored to any desired shade or hue with any type of colorant, such as, for example, pigments, dyes, tints, and the like. Thus, one or more layers of the wound care device may contain a coloring agent. The coloring agent is selected from the group consisting of pigments, dyes, tints, and the like, and combinations thereof.

Antimicrobial and Other Agents

The particular antimicrobial treatment which may be applied to the wound care device of the present invention comprises at least one silver ion-releasing compound selected from the group consisting of silver ion exchange materials (e.g. silver zirconium phosphates, silver calcium phosphates and silver zeolites), silver particles (e.g. silver metal, nanosilver, colloidal silver), silver salts (e.g. AgCl, $Ag_2CO_3$), silver glass, and mixtures thereof. One preferred silver ion-containing compound is an antimicrobial silver sodium hydrogen zirconium phosphate available from Milliken & Company of Spartanburg, South Carolina, sold under the tradename AlphaSan®. Other potentially preferred silver-containing antimicrobials suitable for use herein— including silver zeolites, such as a silver ion-loaded zeolite available from Sinanen Co., Ltd. of Tokyo, Japan under the tradename Zeomic®, and silver glass, such as those available from Ishizuka Glass Co., Ltd. of Japan under the tradename Ionpure®—may be utilized either in addition to, or as a substitute for, the preferred species listed above. Other silver ion-containing materials may also be used. Various combinations of these silver-containing materials may be made if adjustments to the silver release rate over time are desired.

Generally, the silver-based compound is added in an amount from about 0.01% to about 60% by total weight of the particular finish composition; more preferably, from about 0.05% to about 40%; and most preferably, from about 0.1% to about 30%. The antimicrobial finish itself, including any desired binders, wetting agents, odor absorbing agents, leveling agents, adherents, thickeners, and the like, is added to the substrate in an amount of at least about 0.01% of the total device weight.

A binder material has been found useful in preventing the antimicrobial from flaking onto the wound. Preferably, this component is a polyurethane-based binding agent, although a wide variety of cationic, anionic, and non-ionic binders may also be used, either alone or in combination. Preferably, the binding agent is biocompatible such that is does not cause negative reactions in the wound. In essence, such binders provide durability by adhering the antimicrobial to the target substrate, such as fibers or fabrics, without negatively affecting the release of silver ions to the wound.

Total add-on levels of silver to the target substrate may be 20 ppm or higher. More preferably, total add-on levels of silver may be 200 ppm or higher. Although an upper boundary limit of silver add-on levels to the target substrate has not been determined, consideration of the manufacturing economics and the potential to irritate a sensitive wound site suggests avoiding excessive silver levels.

Application of Antimicrobial and Other Agents to Substrate

Silver ion-containing compounds (such as AlphaSan®, Zeomic®, or Ionpure®) may be admixed in an aqueous dispersion with a binder to form a bath into which the target substrate is immersed. Other similar types of compounds that provide silver ions may also be utilized.

When specific polyurethane-based binder materials are utilized, the antimicrobial characteristics of the treated substrate are effective with regard to the amount of surface available silver that is released to kill bacteria, without altering the color of the treated substrate (that is, while substantially maintaining its original appearance). While it currently appears that the use of polyurethane-based binder resins are preferred due to their allowance of silver release and bio-neutral properties, in practice essentially any effective cationic, anionic, or non-ionic binder resin that is not toxic to the wound may be used.

An acceptable method of providing a durable antimicrobial silver-treated fabric surface is the application of a silver ion-containing compound and polyurethane-based binder resin from a bath mixture. This mixture of antimicrobial compound and binder resin may be applied through any technique as is known in the art, including spraying, dipping, padding, foaming, printing, and the like. By using one or more of these application techniques, a fabric may be treated with the antimicrobial compound and binder resin on only one side of the fabric (e.g. the wound contact surface of a wound care device), or it may be treated on both sides of the fabric.

The wound care device may then be cut into any geometric shape or size depending upon its end-use application. The wound care device may be cut using a computer controlled cutting device such as a Gerber machine. It may also be cut using a mechanical dye cutter, hot knife, straight blade, or rotary blade. The wound care device may be cut into any size, such as, for example, a square, rectangle, triangle, circle and the like. The length of the wound care device may be 1", 2", 3", 4", 5", 6", 7", and the like and longer. The width may be 1", 2", 3", 4", 5", 6", 7", and the like and longer. The wound care device may be comprised of any combination of length and width. In one aspect, the wound care device may be 2" by 2", 2" by 3", 3" by 3", 4" by 2", 4" by 3", 4" by 4", or 4" by 5" in size. The wound care device may also be of any variety of whimsical shapes, such as, dog bone shape, heart shape, smiley face, or any other shape that is desired. The wound care device may also be sterilized prior to use via a variety of heat, chemical and/or radiation techniques. In one aspect, sterilization may be accomplished via gamma radiation.

Turning to the Figures, FIGS. 1A and 1B illustrate wound care device 101 of the present invention. In consecutive order from wound contact surface to the surface furthest away from the wound, wound care device 101 comprises apertured (or perforated) adhesive layer 102, fluid transport layer 106 having a wound contact (or wound facing) surface 108 and fluid reservoir surface 110, adhesive layer 114, fluid retentive layer 120, adhesive layer 128, and occlusive film layer 130 having an inner surface 132 and an outer surface 134. Apertured adhesive layer 102 contains multiple apertures (e.g. holes or openings) 104.

The fluid transport layer 106 has a first surface 108, which provides a fluid-contacting or skin-facing surface for the wound care device 101, and a second surface 110. Adhesive layer 102 is applied to the first surface 108 of the fluid transport layer 106. The fluid retentive layer 120 has a first surface 122 and second surface 124 and is positioned so that the first surface 122 is adjacent to the fluid reservoir surface 110 of the fluid transport layer 106. Thus, the fluid retentive layer 120 can act as a reservoir for the fluids taken up by the fluid transport layer 106. As depicted in FIGS. 1A and 1B, the fluid transport layer, fluid retentive layer, and, if present, occlusive film layer may be attached to each other using adhesive layers 114,128.

FIGS. 1C and 1D illustrate yet another embodiment of the wound care device of the present invention. In FIGS. 1C and 1D, wound care device 101 is similar to the device of FIGS. 1A and 1B except that wound care device 101 has been inverted in order to better illustrate the alternative embodiments of apertured adhesive layer 102. Herein, FIG. 1C contains wound care device 101 having, in consecutive order from wound contact surface to the surface furthest away from the wound, apertured adhesive layer 102 containing apertures 104, fluid transport layer 106, adhesive layer 114, fluid retentive layer 120, adhesive layer 128, and occlusive film layer 130. The fluid transport layer 106 has a first surface 108, which provides a fluid-contacting or skin-facing surface for the wound care device 101, and a second surface 110. The fluid retentive layer 120 has a first surface 122 and second surface 124, and occlusive film layer 130 has an inner surface 132 and an outer surface 134. FIG. 1C is provided to illustrate that, in one aspect of the invention, apertures 104 may be of an alternative shape and size than that which is illustrated in FIG. 1B. In this instance, apertures 104 include four large squares situated in a uniform arrangement across the surface of apertured adhesive layer 102. Such an arrangement allows for greater contact between the wound site and fluid transport layer 106. FIG. 1D is the same as FIG. 1C, except that apertured adhesive layer 102 is provided as a border (or window) adhesive layer having one large opening in the approximate center of layer 102. FIG. 1D thus illustrates an exemplary configuration of layer 102 which allows for even greater contact between the wound site and fluid transport layer 106.

FIG. 1E illustrates yet another embodiment of the wound care device according to the present invention. FIG. 1E is the same as shown and described for FIG. 1D, except that apertured adhesive layer 102 is shown to be dimensionally larger at its outer edges than all other layers of wound care device 101. This feature creates an outer adhesive border around the remaining layers of the wound care device. While shown to be larger on all four edges in FIG. 1E, it is contemplated to be within the scope of the present invention that apertured layer 102 may be dimensionally larger at its outer edges on one outer edge, on two outer edges, on three outer edges, or on all four outer edges.

As depicted in FIG. 2, fluid transport layer 200 is comprised of hydrophilic fibers 202 and hydrophobic fibers 204 intermeshed together in a jersey knit construction.

FIG. 3A illustrates adhesive layer 102 which is an apertured film having multiple discrete apertures (perforations or discontinuities) 104. FIG. 3B illustrates yet another embodiment of the invention wherein adhesive layer 102 is comprised of three layers of material forming a trilaminate adhesive layer. The trilaminate is formed of layers 102a, 102b and 102c. In one aspect layer 102a is comprised of an acrylic material, layer 102b is comprised of a polyurethane film, and 102c is comprised of silicone adhesive.

As can be seen in FIG. 4, perforated adhesive layer 102 comprises a plurality of discrete apertures (perforations or discontinuities) 104. These apertures preferably have a dimension sufficient to permit the passage of fluid through adhesive layer 102 to the underlying fluid transport layer formed by the yarn(s) 202 and the effect yarn(s) 204.

FIGS. 5 to 9 are photomicrographs of Example 2, described in greater detail later herein. FIG. 5 illustrates multiple apertures present in the adhesive layer of the wound care device of the present invention. Also, illustrated in FIG. 5 is the fiber of the fluid transport layer present in the layer immediately behind/under the adhesive layer. FIG. 5 also illustrates one embodiment of the present invention wherein the apertures in the adhesive layer are present in a substantially uniform pattern. FIG. 6 is a view similar to FIG. 5, but at higher magnification and at a 50 degree angle. FIG. 6 further illustrates the fibers protruding into the apertures of the wound care device. FIG. 7 shows one apertures of the wound care device of the present invention at 80× magnification. Polymer stress lines are evident in FIG. 7 and are believed to be caused from puncturing the adhesive layer to form the apertures. FIG. 8 illustrates the silver-containing compound present on the fibers of the fluid transport layer of the wound care device. FIG. 9 is a magnified cross-sectional view of some of the layers of the wound care device. FIG. 9 illustrates, from top to bottom: the release liner followed by the silicone adhesive layer followed by the fluid transport layer followed by the fluid retentive layer (open-cell polyurethane foam). The lightest colored area along the top surface and the bottom surface of the fluid transport layer is the silver-containing compound. In this embodiment, the silver-containing compound is present on both surfaces of the fluid transport layer. Also illustrated in FIG. 9 is a single aperture.

FIGS. 10 and 11 are photomicrographs of Comparative Example 1, which is described in more detail further herein. FIG. 10 illustrates the multiple apertures present in the adhesive layer of the wound dressing. However, there is no fiber-containing layer contained within this dressing as is apparent by looking at the photomicrographs. Rather, an open-cell foam is present behind/under the adhesive layer. FIG. 10 also illustrates the apertures present in Comparative Example 1 in a non-uniform arrangement/pattern. FIG. 11 is a greater magnified view of the adhesive layer of Comparative Example 1.

FIGS. 12 and 13 are photomicrographs of Comparative Example 3, which is described in more detail further herein. FIG. 12 illustrates the multiple apertures present in the adhesive layer of the wound dressing. However, there is no fiber-containing layer contained within this dressing as is apparent by looking at the photomicrographs. Rather, an open-cell foam is present behind/under the adhesive layer. FIG. 13 is a magnified view of a single aperture present in the adhesive layer of Comparative Example 3.

The following examples further illustrate the present wound care device having fluid transfer properties, but are not to be construed as limiting the invention as defined in the claims appended hereto. All parts and percents given in these examples are by weight unless otherwise indicated.

Sample Creation and Evaluation

A. Substrate Descriptions

The fabric used for Examples 1 and 2 was a jersey knit (circular knit), multi-polymer fabric sold by Milliken & Company. The fabric was single layer of fabric comprised of approximately 66% continuous filament polyamide yarn, 19% continuous filament polyester yarn, and 15% continuous filament spandex yarn. The polyamide yarn was comprised of 2 plies of 40 denier/34 filament count nylon 6 fiber that was exposed to a texturing process prior to knitting. The polyester yarn was comprised of single ply 70 denier/34 filament count fiber that was exposed to a texturing process prior to knitting. The spandex yarn was comprised of 55 denier/3 filament count fiber.

The fabric was knitted in such as manner as to give a distinct nylon side and a distinct polyester side. The polyester side of the fabric was exposed to a face-finishing process known as sanding.

The fabric was passed through a bath containing an antimicrobial formulation (further described below) and subsequently through squeeze rollers to achieve a wet pickup of about 85%. The fabric was then dried in a tenter frame to remove excess liquid.

Silicone Gel Adhesive A was Acrysil™ 150, a trilaminate film comprised of a layer of silicone adhesive, a polyurethane membrane, and a layer of acrylic adhesive. Acrysil™ 150 is commercially available from Zodiac Coating of Pusignan, France. The film contained perforations having a size of less than 1.0 mm.

Silicone Gel Adhesive B was Acrysil™ 150, a trilaminate film comprised of a layer of silicone adhesive, a polyurethane membrane, and a layer of acrylic adhesive. Acrysil™ 150 is commercially available from Zodiac Coating of Pusignan, France. The film contained perforations having a size of about 1.8 mm.

Silicone Gel Adhesive C-1 was P-Derm® PS-2046, a perforated trilaminate film comprised of high adhesion silicone gel skin contact adhesive (1.3N/25 mm), polyurethane, and medical pressure sensitive acrylic. This adhesive has a thickness of 0.22 mm and hole size of 1.5 mm with 17% open space. P-Derm® PS-2046 is commercially available from Polymer Science, Inc. of Monticello, Indiana.

Silicone Gel Adhesive C-2 was P-Derm® PS-2048, a perforated trilaminate film comprised of high initial tack silicone gel skin contact adhesive (1.1N/25 mm), polyurethane, and medical pressure sensitive acrylic. This adhesive has a thickness of 0.22 mm and hole size of 1.5 mm with 17% open space. P-Derm® PS-2048 is commercially available from Polymer Science, Inc. of Monticello, Indiana.

Silicone Gel Adhesive D was Acrysil™ 150, a trilaminate film comprised of a layer of silicone adhesive, a polyurethane membrane, and a layer of acrylic adhesive. Acrysil™ 150 is commercially available from Zodiac Coating of Pusignan, France. Perforations were added to Silicone Gel Adhesive D having a size of about 6.0 mm. [we added the perforations, correct?]

Silicone Gel Adhesive E was Acrysil™ 150 with no perforations.

B. Antimicrobial Coating Formulations

Various dispersions of an antimicrobial finish include combinations of the following components:

Antimicrobial AlphaSan® RC2000 silver-based ion exchange compound, available from Milliken & Company of Spartanburg, SC;

Witcobond® W-293 (67% solids) or Witcobond UCX-281F (40% solids), polyurethane binders available from Chemtura Corporation of Middlebury, CT; and Water.

EXAMPLE 1

Example 1 was comprised of the following sequential layers: Silicone Gel Adhesive A, a jersey knit fabric (described previously, available from Milliken & Company of Spartanburg, SC), a hot melt adhesive (copolyamide, PA1008/1-060-014.25 available from SpunFab), a polyurethane foam (Medisponge® 60P available from Essentra), a hot melt adhesive (copolyamide, PA1008/1-060-014.25 available from SpunFab), and a polyurethane film (Inspire® 2340 available from Coveris). The Inspire® film was printed with logo and product identification. No silver antimicrobial was included.

A layer of hot melt adhesive was laid over the top of the jersey knit fabric. The fabric-hot melt composite was then fed into a laminating machine, along with all the additional layers in the correct order/configuration as outlined above. The machine was set at a temperature of 185° C. and a speed of 2.6 m/min. The laminate product was wound on a take-up roller.

EXAMPLE 2

Example 2 was the same as Example 1, except Silicone Gel Adhesive A was replaced with Silicone Gel Adhesive B.

MODIFIED EXAMPLE 2

Modified Example 2 was the same as Example 2, except individual fibers from the fluid transport layer were pulled through about 10% of the apertures in the silicone adhesive layer using tweezers.

EXAMPLE 3

Example 3 was the same as Example 1, except Silicone Gel Adhesive A was replaced with Silicone Gel Adhesive C-1.

EXAMPLE 4

Example 4 was the same as Example 1, except Silicone Gel Adhesive A was replaced with Silicone Gel Adhesive D.

EXAMPLE 5

Example 5 was the Ultra® foam dressing (available from Milliken & Company of Spartanburg, SC), which was comprised of a layer of Silicone Adhesive B (described previously), a layer of jersey knit fabric (described previously), and a layer of polyurethane foam.

C. Comparative Sample Descriptions

Several commercially available wound care devices were also purchased for evaluation. They include the following:

COMPARATIVE EXAMPLE 1

"Mepilex® Ag", a non-adhesive single layer polyurethane foam dressing that contains silver; available from MöInlycke Health Care AB of Gothenburg, Sweden.

COMPARATIVE EXAMPLE 2

"Mepilex®", a non-adhesive single layer polyurethane foam dressing; available from MöInlycke Health Care AB of Gothenburg, Sweden.

COMPARATIVE EXAMPLE 3

"Allevyn® Gentle", a three-layer adhesive dressing comprised of a top film layer, a polyurethane foam core middle layer, and an adhesive wound contact layer; available from Smith & Nephew of London, United Kingdom.

COMPARATIVE EXAMPLE 4

"Allevyn® Ag", a three-layer adhesive dressing comprised of a top film layer, a silver-containing (silver sulfadiazine) polyurethane foam core middle layer, and an adhesive wound contact layer; available from Smith & Nephew of London, United Kingdom.

COMPARATIVE EXAMPLE 5

"Optifoam® Ag+", a non-adhesive dressing comprised of a silver-containing (ionic silver) polyurethane foam layer and a film layer; available from Medline Industries, Inc. of Mundelein, Illinois.

COMPARATIVE EXAMPLE 6

"Optifoam® Gentle", a silicone adhesive dressing comprised of a silicone adhesive layer, a polyurethane foam layer, and a film layer; available from Medline Industries, Inc. of Mundelein, Illinois.

COMPARATIVE EXAMPLE 7

"Cutimed® Siltec", a silicone adhesive dressing comprised of a perforated silicone adhesive layer, a polyurethane foam layer that contains superabsorbent particles, and a polyurethane film layer; available from BSN Medical of Hamburg, Germany.

D. Example Testing and Evaluation

Each of the above examples was tested for a variety of characteristics as will be described below. The silicone adhesive of the inventive wound care device was the intended wound contact surface. Further, commercially available products (referred to as Comparative Examples 1-7 and described above) were also tested for comparison with the inventive wound care device. The test procedures will be described in greater detail in the following description. However, a listing of the tests employed is found below.

Test 1. Drop Disappearance Test (internally developed method)
Test 2. Periwound Protection Test (internally developed method)
Test 3. Vertical Leg Model (internally developed method)
Test 4. Vertical Wicking
Test 5. Peel Strength (ASTM D6862-11)
Test 6. Free Swell Bulk Absorption Test (EN 13726-1: 2002, Part 1, Test 3.2:Free Swell Absorptive Capacity)

Test 1: Drop Disappearance Test

The purpose of this test is to measure the amount of time it takes for a single drop of fluid to be absorbed into the substrate. The fluid used was simulated wound fluid. Simulated wound fluid is a solution of deionized water containing 142 mM of sodium chloride and 2.5 mM of calcium chloride. The simulated wound fluid is isotonic to human blood. The simulated wound fluid was contained within a 2 mL syringe. Two millimeters of fluid were dispensed by hand onto the approximate center of the substrate. The time it took for the drop to disappear (to be absorbed into the substrate) was recorded. The test was stopped after 600 seconds was reached. Test results are provided in Table 1.

TABLE 1

Drop Disappearance Properties of Inventive and Comparative Wound Care Devices

| Sample | Time (seconds) |
| --- | --- |
| Example 1 | 600 |
| Example 2 | 8 |
| Example 3 | 15 |
| Example 4 | 34 |
| Example 5 | 5 |
| Comparative Example 1 | 600 |
| Comparative Example 2 | 600 |
| Comparative Example 3 | 13 |
| Comparative Example 4 | n/a |
| Comparative Example 5 | n/a |
| Comparative Example 6 | 120 |

The results shown in Table 1 demonstrate that the inventive wound care device having a perforated adhesive film layer (wound contact surface) with apertures of at least 1.8 mm in size demonstrate the fastest drop disappearance.

Test 2: Periwound Protection Test

The purpose of this test is to measure the amount of moisture or liquid that is transferred from the dressing to the healthy periwound skin. Simulated wound fluid was used. The apparatus was a syringe pump with 1/32" internal diameter tubing attached to a small hole in the center of a petri dish. This simulated the wound. A pre-weighed, 2" diameter piece of two-layer gauze with a 10 mm hole in the center was placed on the petri dish with the tubing hole centered within the hole in the gauze. The gauze simulated the periwound skin. A 2" diameter dressing cutout was placed on top of the gauze and a weight of approximately 42 grams was placed on top of the dressing. Simulated wound fluid was delivered to the "wound" at a rate of 0.2 mL/hr for 24 hours. At the completion of the test, the weight of the gauze was recorded and the percent fluid pick up was determined. Test results are provided in Table 2.

TABLE 2

Periwound Protection of Inventive and Comparative Wound Care Devices

| Sample | Percent Pick Up (%) |
|---|---|
| Example 1 | 842 +/− 402 |
| Example 2 | 68 +/− 42 |
| Example 3 | 13 +/− 3 |
| Example 4 | 40 +/− 51 |
| Example 5 | 51 +/− 21 |
| Comparative Example 1 | 848 +/− 727 |
| Comparative Example 2 | 963 +/− 584 |
| Comparative Example 3 | 729 +/− 97 |
| Comparative Example 6 | 167 +/− 258 |

The results shown in Table 2 demonstrate that the inventive wound care device having a perforated adhesive film layer (wound contact surface) with apertures of at least 1.5 mm in size demonstrated a lower percent pick up and therefore greater periwound protection.

Test 3: Vertical Leg Model Test

The purpose of this test is to measure the amount of fluid that is absorbed by the wound care device over a period of time in a vertical orientation prior to failure. The fluid used was simulated wound fluid. Failure is defined as the point in time when the wound care device either (a) started to peel from the nylon surface of the leg model or completely fell off the leg model, or (b) started to leak simulated wound fluid from the edges and/or borders of the wound care device. Samples were run at 24 mL/hour until failure. Test results are provided in Table 3.

TABLE 3

Vertical Leg Test Properties of Inventive and Comparative Wound Care Devices

| Sample | Fluid Absorbed (mL) |
|---|---|
| Example 1 | 47 |
| Example 2 | 46 |
| Example 3 | 44 |
| Example 4 | n/a |
| Comparative Example 1 | 18 |
| Comparative Example 2 | n/a |
| Comparative Example 3 | 19 |
| Comparative Example 4 | n/a |
| Comparative Example 5 | n/a |
| Comparative Example 6 | 43 |
| Comparative Example 7 | 14 |

The results shown in Table 3 demonstrate that the inventive wound care device having a perforated adhesive film layer (wound contact surface) with apertures of at least 1.5 mm in size demonstrated a significant amount of fluid absorption in a vertical orientation prior to failure.

Test 4: Vertical Wicking Test

The purpose of this test is to measure the amount of fluid that is absorbed by the wound care device over a certain period of time in a vertical orientation. The fluid used was simulated wound fluid. Each sample was tested in triplicate. The average and standard deviation was calculated and is presented in Table 4.

TABLE 4

Vertical Wicking Properties of Inventive and Comparative Wound Care Devices

| Sample | Fluid Absorbed (mL) | | | | | |
|---|---|---|---|---|---|---|
| | At 10 seconds | At 20 seconds | At 30 seconds | At 40 seconds | At 50 seconds | At 60 seconds |
| Example 1 | n/a | n/a | n/a | n/a | n/a | n/a |
| Example 2 | 2.30 +/− 0.00 | 2.60 +/− 0.10 | 3.12 +/− 0.16 | 3.43 +/− 0.24 | 3.82 +/− 0.15 | 4.00 +/− 0.00 |
| Example 3 | 2.27 +/− 0.15 | 3.02 +/− 0.14 | 3.53 +/− 0.21 | 3.87 +/− 0.23 | 4.00 +/− 0.00 | 4.00 +/− 0.00 |
| Example 4 | n/a | n/a | n/a | n/a | n/a | n/a |
| Example 5 | 2.43 +/− 0.15 | 3.27 +/− 0.08 | 3.83 +/− 0.06 | 4.00 +/− 0.00 | 4.00 +/− 0.00 | 4.00 +/− 0.00 |
| Comparative Example 1 | 1.40 +/− 0.10 | 1.47 +/− 0.06 | 1.47 +/− 0.06 | 1.50 +/− 0.00 | 1.50 +/− 0.00 | 1.53 +/− 0.06 |
| Comparative Example 2 | 0.97 +/− 0.21 | 1.08 +/− 0.18 | 1.25 +/− 0.05 | 1.37 +/− 0.08 | 1.50 +/− 0.13 | 1.60 +/− 0.05 |
| Comparative Example 3 | 1.17 +/− 0.06 | 1.25 +/− 0.05 | 1.37 +/− 0.06 | 1.43 +/− 0.03 | 1.57 +/− 0.08 | 1.68 +/− 0.08 |
| Comparative Example 4 | n/a | n/a | n/a | n/a | n/a | n/a |
| Comparative Example 5 | n/a | n/a | n/a | n/a | n/a | n/a |
| Comparative Example 6 | 1.68 +/− 0.03 | 1.93 +/− 0.06 | 2.63 +/− 0.03 | 2.90 +/− 0.00 | 3.13 +/− 0.03 | 3.33 +/− 0.03 |
| Comparative Example 7 | n/a | n/a | n/a | n/a | n/a | n/a |

The results shown in Table 4 demonstrate that the inventive wound care device having a perforated adhesive film layer (wound contact surface) with apertures of at least 1.5 mm in size demonstrates a significant wicking ability in the vertical direction.

Test 5: Peel Strength Test

The purpose of this test is to measure the amount of force it takes to remove the wound care device from the surface of stainless steel. Each sample was applied to the surface according to the product directions. Removal of the sample was done by a testing machine with a load weighing system. The force required to remove each sample was recorded in grams of force (gf).

Test results are provided in Table 5.

TABLE 5

Peel Strength of Inventive and Comparative Wound Care Devices

| Sample | Peel Strength (gf) |
| --- | --- |
| Example 5 | 193.640 |
| Comparative Example 1 | 87.662 |
| Comparative Example 2 | 87.361 |
| Comparative Example 3 | 106.931 |
| Comparative Example 6 | 274.968 |

The results shown in Table 5 demonstrate that the amount of force needed to remove the inventive wound care device from the stainless steel surface is found in between the amount of force needed for removal of the Comparative Examples.

Test 6: Free Swell Bulk Absorption Test

The purpose of this test is to measure the absorptive capacity of a dressing. The weight of a 5 cm by 5 cm sample of dressing was recorded. The sample of dressing was added to a dish with a quantity of 37° C. simulated wound fluid that was approximately 40 times the weight of the dressing. The dressing was allowed to sit in the fluid for 30 min at 37° C. At the end of the test the sample was suspended for 30 seconds and weighed. The absorptive capacity of the sample was determined. Each sample was tested in triplicate. The average and standard deviation was calculated and is presented in Table 6.

TABLE 6

Free Swell Bulk Absorption Properties of Inventive and Comparative Wound Care Devices

| Sample | Absorptive Capacity (g/cm$^2$) |
| --- | --- |
| Example 1 | 6341 +/− 47 |
| Example 2 | 5791 +/− 232 |
| Example 3 | 6140 +/− 328 |
| Example 4 | 5013 +/− 423 |
| Example 5 | 5176 +/− 90 |
| Comparative Example 1 | 7025 +/− 465 |
| Comparative Example 2 | 7837 +/− 463 |
| Comparative Example 3 | 4690 +/− 267 |
| Comparative Example 6 | 5269 +/− 60 |
| Comparative Example 7 | 9174 +/− 176 |

The results shown in Table 6 demonstrate that the inventive wound care device having a perforated adhesive film layer (wound contact surface) exhibits comparable absorptive capacity to the Comparative Examples.

Test 7: Antimicrobial Efficacy

Antimicrobial efficacy against both Gram-positive (e.g. *Staphylococcus aureus* ATCC #6538) and Gram-negative (e.g. *Klebsiella pneumoniae* ATCC #4352) bacteria was measured for inventive and comparative wound care devices. The quantitative reduction of bacteria after exposure to the samples versus the control was assessed using a modified version of AATCC Method 100.

Portions of each wound dressing sample (non-sterile 15 mm diameter disks) were placed into 24-well microplates. With all samples, the dressings were placed with the side down that normally contacts the wound. Overnight cultures of the test microbes were suspended in 5% nutrient broth in saline ca. 10E6 cells/ml. At time 0, each sample was pre-soaked in sterile saline via immersion. The wells of the 24 well plate were inoculated with bacteria (0.1 ml of ca. 10E6 cells/nil) and then the sample was placed contact side down in the inoculum. The 24 well plates were then incubated at 37° C. After incubation for 24 hours, the samples were removed and placed into 50 ml centrifuge tubes filled with 5 ml of a "wash solution" (Tryptic Soy Broth+0.7% Tween 80+0.1% cysteine (to inactivate residual silver)). After vortexing to remove attached cells, the number of viable cells in the solution was quantified using a microtiter plate-based "Most-Probable Number" assay. The recipe for full-strength Nutrient Broth indicated in this method is 5 g/l peptone and 3 g/l beef extract. Duplicate samples were tested against *Staphylococcus aureus* ATCC#6538 and *Klebsiella pneumoniae* ATCC #4352.

The Control sample was Ultra® foam dressing (available from Milliken & Company of Spartanburg, SC) which does not contain a silicone adhesive layer. The results are shown in Table 7 and FIG. 14.

TABLE 7

Antimicrobial Efficacy Against Gram-Positive and Gram-Negative Bacteria vs. Control

| Sample ID | Average Log Reduction vs. Control Against *Klebsiella pneumoniae* | Average Log Reduction vs. Control Against *Staphylococcus aureus* |
| --- | --- | --- |
| Example 1 (<1.0 mm apertures) | 3.66 +/− 0.18 | 2.36 +/− 0.90 |
| Example 2 (1.8 mm apertures) | 4.31 +/− 0.59 | 2.83 +/− 0.67 |
| Modified Example 2 (1.8 mm apertures, fiber pull-through) | 3.49 +/− 0.35 | 2.68 +/− 0.04 |
| Example 3 (1.5 mm apertures) | 3.98 +/− 0.27 | 2.61 +/− 0.07 |
| Comparative Example 1 | 4.31 +/− 0.59 | 2.98 +/− 0.45 |
| Control (silver, but no silicone) | 6.02 +/− 0.18 | 4.00 +/− 0.24 |

The results in Table 7 and FIG. 14 indicate that the inventive wound care devices exhibit antimicrobial efficacy against both Gram-positive and Gram-negative bacteria. The antimicrobial efficacy is comparable to other commercially available silver-containing wound care devices (Comparative Example 1). Examples 1 to 3 exhibited at least 50% of the antimicrobial efficacy shown by the control sample (no silicone adhesive layer). In this instance, the data may be interpreted to illustrate that the antimicrobial efficacy is reduced by less than 50% when a silicone adhesive layer is included in the wound care device. Some of Examples 1 to 3 exhibited at least 70% of the antimicrobial efficacy shown by the control sample (no silicone adhesive layer). In this instance, the data may be interpreted to illustrate that the antimicrobial efficacy is reduced by less than 30% when a silicone adhesive layer is included in the wound care device.

For this testing, *Klebsiella pneumoniae* was selected as the representative Gram-negative microbe and *Staphylococcus aureus* was selected as the representative Gram-positive microbe. However, it should be understood to be within the scope of this invention that the wound care device of the present invention would exhibit similar antimicrobial efficacy against other Gram-positive and Gram-negative bacteria, as well as against fungi such as *C. albicans*.

Additional test methods useful for analyzing the wound care device of the present invention are as follows:
   Test 8. Fluid Transport Test (Internally developed method)
   Test 9. Tensile Strength Test (ASTM D 5034)
   Test 10. Zone of Inhibition Test (Kirby-Bauer Agar Diffusion Assay)
   Test 11. Total AlphaSan® RC 2000 Content Test (Ashing Technique)
   Test 12. Conductivity/Resistivity Test (AATCC Test Method 76)
   Test 13. Thickness Test (ASTM D 1777-96)

Many of these tests were conducted in commonly owned U.S. Pat. Nos. 7,842,306; 8,021,685, and 8,394,403, all of which are incorporated by reference herein.

Test 8: Fluid Transport Test

The purpose of this test is to measure the amount of fluid that is transported from the wound contact side of the wound care device (Side A) to the non-wound contact side of the device (Side B). The test also attempts to measure the amount of fluid pushed back to the wound contact side of the device (Side A).

Simulated wound fluid ("SWF") was prepared by adding 16.60 g NaCl and 0.56 g $CaCl_2$ to a 2 L volumetric flask. The flask was then filled to volume (2000 mL total) with deionized water. The flask was then capped and shaken until all of the salts were completely dissolved. The simulated wound fluid is comprised of 0.142M (142 mM) NaCl (aq) and 0.0025M (2.5 mM) $CaCl_2$ (aq).

A test sample of a wound care device (5 cm in diameter) was placed onto a polypropylene disc (5 cm in diameter). Twenty drops of simulated wound fluid was added to Side A of the test sample using a dropper. The test sample was allowed to rest in a horizontal position for 2 minutes. The test sample was then sandwiched in a vertical position between two discs of filter paper (Whitman filter paper 3, diameter=110 mm) using a clamp—Filter Paper A contacted Side A of the test sample and Filter Paper B contacted Side B of the test sample. The test sample was held in this position for 5 seconds. It was determined that the clamp exerts a pressure of 340 mm Hg.

Filter papers A and B had been weighed prior to the test. They were then weighed after the test and difference in weight was determined. This weight difference provides a calculation of the amount of SWF transferred from the wound care device to Filter Paper A and/or B.

The SWF was added to the polyester side ("Side A") of the wound care device of the present invention. SWF was added to the wound contact side of competitive dressings, as directed by the product brochures.

The values are provided as "percent weight change." The percent weight change represents the weight of the fluid absorbed relative to the dry weight of the filter paper. It is calculated by subtracting the weight of the dry filter paper (grams) from the weight of the wet filter paper (grams) and dividing this difference by the weight of the dry filter paper. This value is then multiplied by 100.

Test 9: Tensile Strength

Tensile strength (grab) of various wound care devices was determined using ASTM D 5034. The purpose of this test is to determine structural integrity of wet and dry wound care devices. The devices were wetted by dipping them in simulated wound fluid (same formulation as described previously). Measurements are shown in pounds of force (lbf). Higher values indicate that more force was needed to tear the sample.

Test 10: Zone of Inhibition Test

Zone of Inhibition testing may be conducted to determine the antimicrobial activity of various wound care devices against several microbes using a modified version of the Kirby-Bauer Susceptibility Test. A brief description of the test method is included below. A full description of the test method may be found in the following document: National Committee for Clinical Laboratory Studies (NCCLS) M2-A8: Performance Standards for Antimicrobial Disk Susceptibility Tests; Approved Standard—Eighth Edition; 2003.

Several Gram-positive and Gram-negative bacteria as well as fungi (yeast) may be chosen to illustrate the antimicrobial efficacy of the inventive wound care device. Gram-positive bacteria include, for example and without limitation, *Staphylococcus aureus, Clostridium perfringens, Enterococcus faecium* and *Bacillus cereus*. Gram-negative bacteria include, for example and without limitation, *Klebsiella pneumoniae, Escherichia coli, Acinetobacter baumannii, Enterobacter cloacae, Proteus mirabilis*, and *Pseudomonas aeruginosa*. Fungi, such as yeast, include for example, *Candida albicans* and *Saccharomyces cerevisiae*.

An overnight culture of the test microbe was diluted into saline (0.85% NaCl) to a concentration of $10^6$ cells/ml. Petri dishes containing Diagnostic Sensitivity Test (DST) Agar were inoculated with 0.25 ml of the cell suspension and incubated for 1 hour. A sample (15 mm diameter circle) of each wound care device was then placed at the center of the agar plate. The agar plate was incubated for 24 hours at 37° C. After measuring the extent of the zones (in mm), the samples were transferred to a fresh DST plate inoculated with the same microbe. The process was repeated for three days (total).

Test 11: Total AlphaSan® Content

Total ALPHASAN® Content Test

The amount of AlphaSan® antimicrobial incorporated into or onto an article can be determined by measurement of elements unique to the antimicrobial compound. For AlphaSan® antimicrobial, the two elements of highest abundance are silver or zirconium. Because zirconium is more abundant in the AlphaSan® antimicrobial product and is easier to measure, it is preferable to use zirconium as the signature element for determining the level of AlphaSan® antimicrobial in an article. The amount of AlphaSan® antimicrobial incorporated into or onto the wound care device was determined using the following ashing technique.

A sample of fabric (weighing approximately 1 gram but with weight measured to four significant digits) was placed in a clean, dry ceramic crucible which had been weighed. The crucible containing the fabric sample was placed in a muffle furnace whose temperature ramped up at 3° C./minute to 750° C. The temperature was then held at 750° C. for four hours. The system was then cooled and the crucible transferred to a desiccator in which it was allowed to reach an equilibrium temperature. The crucible was then weighed. This provides the percent solids of inorganic constituents.

The fabric sample was then ground in the ceramic crucible to obtain a uniform sample. Approximately 0.05 g weight (again measured to four significant digits) was then taken from the ceramic crucible and placed in a platinum crucible. Four milliliters of 50% $HNO_3$, followed by 15-20 drops of 48% HF, were added to the crucible. The crucible was heated over a hot plate until the sample completely dissolved. The sample solution was then transferred to a 100 mL volumetric flask.

The crucible was then rinsed with 5% $HNO_3$, with the rinse solution being added to the flask. The solution was diluted to the 100 mL mark with 5% $HNO_3$. The dilute solution was transferred to a polyethylene storage container. Analysis for the desired active ingredient (in this case, zirconium) was performed using an Inductively Coupled Plasma Optical Emission Spectrometer device (e.g., a Perkin Elmer Optima 4300DV). Calculations are apparent to one skilled in the art. The amount of AlphaSan® RC2000 present on the wound care device is provided as a weight percent based on the weight of the fabric.

Test 12: Conductivity/Resistivity Test

The purpose of this test is to determine the conductivity and resistivity (R) of the inventive wound care device. The test was performed according to AATCC Test Method 76.

Test 13: Thickness Test

The purpose of this test was to measure the thickness of the inventive wound care device. The test was performed according to ASTM D 1777-96.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

We claim:

1. A method for managing moisture at a wound site comprising the steps of:
    (a) providing a wound care device comprising:
        (i) a perforated trilaminate silicone adhesive layer containing apertures;
        (ii) a single layer of fabric having a wound contact surface and a wound fluid reservoir surface, wherein said wound contact surface is comprised primarily of hydrophobic fiber and said wound fluid reservoir surface is comprised primarily of hydrophilic fiber, said hydrophobic and hydrophilic fibers being intermeshed together in a jersey knit fabric construction; and
        (iii) a fluid retentive layer; and
        wherein said wound care device transports wound fluid uni-directionally from said wound contact surface to said wound fluid reservoir surface upon exposure to a wound;
    (b) placing said wound contact surface of said single layer of fabric in contact with said wound site, wherein contact occurs via the apertures of the perforated trilaminate silicone adhesive layer; and
    (c) allowing said wound care device to transport wound fluid uni-directionally from said wound contact surface to said wound fluid reservoir surface.

2. The method of claim 1, wherein said wound contact surface is coated with a composition comprising at least one silver ion-containing compound.

3. The method of claim 1, wherein said perforated trilaminate silicone adhesive layer is comprised of a layer of skin contact silicone, a polyurethane material, and a pressure sensitive acrylic material.

4. The method of claim 1, wherein said perforated trilaminate silicone adhesive layer includes apertures having a size in the range from about 0.1 mm to about 7 mm.

5. The method of claim 1, wherein said perforated trilaminate silicone adhesive layer exhibits a percentage of open area in the range from about 5 percent to about 95 percent.

6. The method of claim 2, wherein said at least one silver ion-containing compound is selected from the group consisting of silver ion exchange materials, silver particles, silver salts, silver glass, and mixtures thereof.

7. The method of claim 6, wherein said silver ion exchange material is selected from the group consisting of silver zirconium phosphate, silver calcium phosphate, silver zeolite, and mixtures thereof.

8. The method of claim 7, wherein said silver ion exchange material is silver zirconium phosphate.

9. The method of claim 2, wherein said composition further comprises a binding agent selected from the group consisting of polyurethane binders, acrylic binders, and mixtures thereof.

10. The method of claim 9, wherein said binding agent is a polyurethane-based material.

11. The method of claim 2, wherein said wound contact surface is non-electrically conductive.

12. The method of claim 1, wherein said hydrophobic fiber is polyester fiber.

13. The method of claim 1, wherein said hydrophilic fiber is polyamide fiber.

14. The method of claim 1, wherein said single layer of fabric further comprises an elastomeric fiber.

15. The method of claim 1, wherein said wound contact and said fluid reservoir surfaces are coated with a composition comprising at least one silver ion-containing compound.

16. The method of claim 15, wherein said wound care device exhibits antimicrobial efficacy.

17. The method of claim 16, wherein said wound care device is non-electrically conductive.

18. The method of claim 1, wherein said single layer of fabric and said perforated trilaminate silicone adhesive layer have approximately the same length and width.

* * * * *